(12) United States Patent
Hashimoto et al.

(10) Patent No.: US 8,338,460 B2
(45) Date of Patent: Dec. 25, 2012

(54) 2-PYRIDINECARBOXAMIDE DERIVATIVE HAVING GK-ACTIVATING EFFECT

(75) Inventors: Noriaki Hashimoto, Ushiku (JP); Yufu Sagara, Tsukuba (JP); Masanori Asai, Tsukuba (JP); Teruyuki Nishimura, Ushiku (JP)

(73) Assignee: MSD K. K., Tokyo (JP)

( * ) Notice: Subject to any disclaimer, the term of this patent is extended or adjusted under 35 U.S.C. 154(b) by 981 days.

(21) Appl. No.: 11/973,240

(22) Filed: Oct. 5, 2007

(65) Prior Publication Data

US 2008/0090799 A1  Apr. 17, 2008

Related U.S. Application Data

(60) Provisional application No. 60/853,812, filed on Oct. 24, 2006.

(30) Foreign Application Priority Data

Oct. 6, 2006   (JP) ................................. 2006-275824

(51) Int. Cl.
  *A61K 31/433*  (2006.01)
  *A61K 31/4439*  (2006.01)
  *C07D 417/14*  (2006.01)
  *C07D 417/10*  (2006.01)

(52) U.S. Cl. .................................. 514/342; 546/268.7

(58) Field of Classification Search ............... 514/210.2, 514/236.2, 318, 342; 546/268.7, 194
See application file for complete search history.

(56) References Cited

U.S. PATENT DOCUMENTS

| | | | |
|---|---|---|---|
| 7,390,908 B2 | 6/2008 | Boyd et al. |
| 7,432,287 B2 | 10/2008 | Iino et al. |
| 7,524,957 B2 | 4/2009 | Boyd et al. |
| 2005/0080106 A1 | 4/2005 | Boyd et al. |
| 2006/0258701 A1 | 11/2006 | Mitsuya et al. |
| 2008/0207636 A1 | 8/2008 | Boyd et al. |

FOREIGN PATENT DOCUMENTS

| | | |
|---|---|---|
| EP | 1 529 530 | 5/2005 |
| EP | 1 568 367 | 8/2005 |
| EP | 1 661 563 | 5/2006 |
| EP | 1 661 567 | 5/2006 |
| EP | 1 661 568 | 5/2006 |
| EP | 1 661 569 | 5/2006 |
| EP | 1 669 068 | 6/2006 |
| EP | 1 669 069 | 6/2006 |
| EP | 1 674 097 | 6/2006 |
| EP | 1 695 705 | 6/2006 |
| EP | 2077266 | 7/2009 |
| GB | 2 277 930 | 11/1994 |
| SE | 010276-8 | 6/2006 |
| WO | 99/24404 A1 | 5/1999 |
| WO | WO 03/000267 | 1/2003 |
| WO | WO 03/015774 | 2/2003 |
| WO | WO 2004/076420 | 9/2004 |
| WO | WO 2004/081001 | 9/2004 |
| WO | 2005/012256 A1 | 2/2005 |
| WO | 2005/042524 A1 | 5/2005 |
| WO | 2005/118579 A2 | 12/2005 |
| WO | 2007/027734 A2 | 3/2007 |
| WO | 2007/052882 A1 | 5/2007 |
| WO | 2007/093542 A1 | 8/2007 |
| WO | 2007/125110 A1 | 11/2007 |

OTHER PUBLICATIONS

Dorwald F. A. Side Reactions in Organic Synthesis, 2005, Wiley: VCH, Weinheim pg. IX of Preface. (Reference enclosed).*
D. Garfinkel et al., "Computer modeling identifies glucokinase as glucose sensor of pancreatic beta-cells", American Journal Physiology, vol. 247, pp. 527-536 (1984).
A. Grupe et al., "Transgenic Knockouts Reveal a Critical Requirement for Pancreatic beta Cell Glucokinase in Maintaining Glucose Homeostasis", Cell, vol. 83, pp. 69-78 (1995).

(Continued)

*Primary Examiner* — Sabiha Qazi
(74) *Attorney, Agent, or Firm* — Anna L. Cocuzzo; John C. Todaro

(57) ABSTRACT

Compounds of a formula (I) and their pharmaceutically-acceptable salts are disclosed. The compounds have glucokinase-activating effect and are therefore useful for treatment of diabetes and obesity.

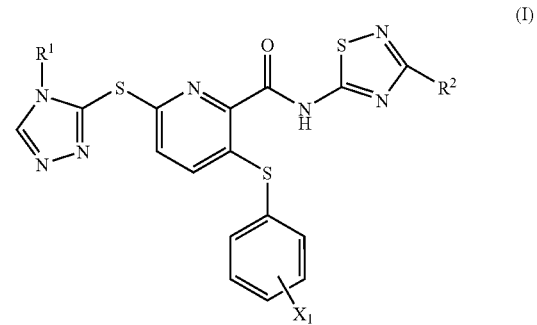

(I)

$R^1$ and $R^2$ each independently represent a lower alkyl group; $X_1$ represent a group of a formula (II-1):

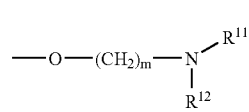

(II-1)

wherein:
$R^{11}$ and $R^{12}$ each independently represent a hydrogen atom or a lower alkyl group, or taken together with the nitrogen atom to which they bond, $R^{11}$ and $R^{12}$ may form a 4- to 7-membered nitrogen-containing aliphatic ring (one carbon atom constituting the 4- to 7-membered nitrogen-containing aliphatic ring may be replaced by an oxygen atom), or taken together with a carbon atom in $(CH_2)_m$, $R^{11}$ and $R^{12}$ may form a 4- to 7-membered nitrogen-containing aliphatic ring; m indicates an integer of from 1 to 3.

3 Claims, No Drawings

OTHER PUBLICATIONS

T. Ferre et al.m "Correction of diabetic alterations by glocokinase", Proceedings of the National Academy of Sciences of the USA, vol. 93, pp. 7225-7230 (1996).

N. Vionnet et al., "Nonsense mutation in the glucokinase gene causes early-onset non-insulin-dependent diabetes mellitus", Nature, vol. 356, pp. 721-722 (1992).

B. Glaser et al., "Familial Hyperinsulinism Caused by an Activating Glucokinase Mutation", New England Journal of Medicine, vol. 338, pp. 226-230 (1998).

T. Ferre et al.m "Correction of diabetic alterations by glucokinase", Proceedings of the National Academy of Sciences of the USA, vol. 93, pp. 7225-7230 (1996).

S. W. Kaldor et al., "Viracept (Nelfinavir Mesylate, AG1343): A Potent, Orally Bioavailable Inhibitor of HIV-1 Protease", J. Med. Chem., vol. 40, pp. 3979-3985 (1997).

N. Zheng et al., "Palladium-Catalyzed Synthesis of Aryl Sulfides from Aryl Triflates", J. Org. Chem., vol. 63, pp. 9606-9607 (1998).

G. Y. Li et al., "Highly Active, Air-Stable Versatile Palladium Catalysts for the C-C, C-N, and C-S Bond Formations via Cross-Coupling Reactions of Aryl Chlorides", J. Org. Chem., vol. 66, pp. 8677-8681 (2001).

U. Schopfer et al., "A general palladium-catalysed synthesis of aromatic and heteroaromatic thioethers", Tetrahedron, vol. 57, pp. 3069-3073 (2001).

T. Migita et al., "The Palladium Catalyzed Nucleophilic Substitution of Aryl Halides by Thiolate Anions", Bull. Chem. Soc. Japan, vol. 53, pp. 1385-1389 (1980).

F. Y. Kwong et al., "A General, Efficient, and Inexpensive Catalyst System for the Coupling of Aryl Iodides adn Thiols", Organic Letters, vol. 4, No. 20, pp. 3517-3520 (2002).

S. Rajagopalan et al., "Synthesis of N-t-BOC-4-S-t-Butyl-L-Thiophenylalanine Via Pallidium Catalyzed Cross-Coupling Reaction of N-t-BOC-4-IODO-L-Phenylalanine with t-Butylthiol or Sodium t-Butylthiolate", Synthetic Communications, vol. 26, No. 7, pp. 1431-1440 (1996).

J. E. T. Corrie et al., "Synthesis of a Cephalosporin Analogue", Journal of Chemical Society, Perkin Transaction, Chapter I, p. 1421-1425 (1977).

S. Sakakibara et al., "Use of Anhydrous Hydrogen Fluoride in Peptide Synthesis. I. Behavior of Various Protective Groups in Anhydrous Hydrogen Fluoride", Bulletin of the Chemical Society of Japan, vol. 40, pp. 2164-2167 (1967).

D. A. J. Ives, "Electrolysis in liquid ammonia solution in peptide chemistry", Canadian Journal of Chemistry, vol. 47, pp. 3697-3699 (1969).

A. Ogawa et al., "Highly Regio- and Stereocontrolled Synthesis of Vinyl Sulfides via Transition-Metal-Catalyzed Hydrothiolation of Alkynes with Thiols", J. Am. Chem. Soc., vol. 121, pp. 5108-5114 (1999).

* cited by examiner

2-PYRIDINECARBOXAMIDE DERIVATIVE HAVING GK-ACTIVATING EFFECT

CROSS-REFERENCE TO RELATED APPLICATIONS

This application is related to Japanese Provisional Application No. JP 2006-275824 filed Oct. 6, 2006 and U.S. Provisional Application No. 60/853,812, filed Oct. 24, 2006, priority which is claimed hereunder.

BACKGROUND OF THE INVENTION

The present invention relates to a glucokinase activator comprising a 2-pyridinecarboxamide derivative as the active ingredient thereof. Further, it relates to a novel 2-pyridinecarboxamide derivative.

Glucokinase (GK) (ATP: D-hexose 6-phosphotransferase, EC 2.7.1.1) is one (hexokinase IV) of four mammal hexokinases. Hexokinase is a first-stage enzyme in glycolysis and catalyzes a reaction from glucose to glucose hexaphosphate. In its expression, glucokinase is limited essentially in liver and pancreas beta cells, and it controls the rate-limiting step of glucose metabolism in these cells thereby playing an important role in systemic saccharometabolism. Glucokinase in liver and that in pancreas beta cells differ from each other in point of the N-terminal 15-amino acid sequence owing to the difference in splicing therebetween, but they are the same in point of the enzymatic property. The enzymatic activity of the other three hexokinases (I, II, III) except glucokinase is saturated at a glucose concentration of at most 1 mM, but Km of glucokinase to glucose is 8 mM and is near to a physiological blood glucose level. Therefore, in accordance with the blood glucose level change from a normal blood glucose level (5 mM) to an increased blood glucose level after meals (10 to 15 mM), intercellular glucose metabolism is accelerated via glucokinase.

Since ten years ago, a hypothesis that glucokinase may act as a glucose sensor in pancreas beta cells and liver has been proposed (for example, see Non-Patent Reference 1). A result of recent glucokinase gene-manipulated mice has confirmed that glucokinase actually plays an important role in systemic glucose homeostasis. Mice in which the glucokinase gene was disrupted die soon after their birth (for example, see Non-Patent Reference 2), but on the other hand, normal or diabetic mice in which glucokinase was excessively expressed have a lowered blood glucose level (for example, see Non-Patent Reference 3). With the increase in glucose concentration therein, the reaction of pancreas beta cells and that of liver cells are both toward the reduction in a blood glucose level, though differing from each other. Pancreas beta cells come to secrete more insulin, and liver takes up sugar to store it as glycogen therein and simultaneously reduces sugar release.

To that effect, the change in the enzymatic activity of glucokinase plays an important role in mammal glucose homeostasis via liver and pancreas beta cells. In a juvenile diabetic case that is referred to as MODY2 (maturity-onset diabetes of the young), mutation of a glucokinase gene has been found, and the glucokinase activity reduction causes the blood glucose level increase (for example, see Non-Patent Reference 4). On the other hand, a pedigree having mutation of increasing glucokinase activity has been found, and those of the family line show low blood glucose level symptoms (for example, see Non-Patent Reference 5).

From these, glucokinase acts as a glucose sensor and plays an important role in glucose homeostasis also in humans. On the other hand, blood glucose level control by utilizing a glucokinase sensor system may be possible in many type-II diabetes patients. A glucokinase-activating substance may be expected to have an insulin secretion promoting effect in pancreas beta cells and have a sugar take-up accelerating and sugar release inhibiting activity in liver, and therefore it may be useful as a remedy for type-II diabetes patients.

Recently, it has become clarified that pancreas beta cell-type glucokinase is limitedly expressed locally in rat brains, especially in ventromedial hypothalamus (VMH) thereof. About 20% neurocytes in VMH are referred to as glucose-responsive neutrons, and heretofore it has been considered they may play an important role in body weight control. When glucose is administered to a rat brain, then it reduces the amount of ingestion; but when glucose metabolism is retarded through intracerebral administration of glucosamine, a glucose analogue, then it causes hyperphagia. From an electrophysiological experiment, it is admitted that glucose-responsive neurons are activated in accordance with a physiological glucose concentration change (5 to 20 mM), but when glucose metabolisms is inhibited by glucosamine or the like, then their activity is retarded. In the glucose concentration-sensitive system in VHM, a glucose-mediated mechanism is anticipated like the insulin secretion in pancreas beta cells. Accordingly, there may be a possibility that a substance for glucokinase activation in VHM, in addition to liver and pancreas beta cells, may be effective not only for blood glucose level correction but also for solution of obesity that is problematic in many type-II diabetes patients.

From the above description, a compound having a glucokinase-activating effect is useful for remedies and/or preventives for diabetes, or for remedies and/or preventives for chronic complications of diabetes such as retinopathy, nephropathy, neurosis, ischemic cardiopathy, arteriosclerosis, and further for remedies and/or preventives for obesity.

For compounds similar to 2-pyridinecarboxamide derivatives of the invention in point of their structure, for example, a compound of the following formula (A) is disclosed (see Patent Reference 1):

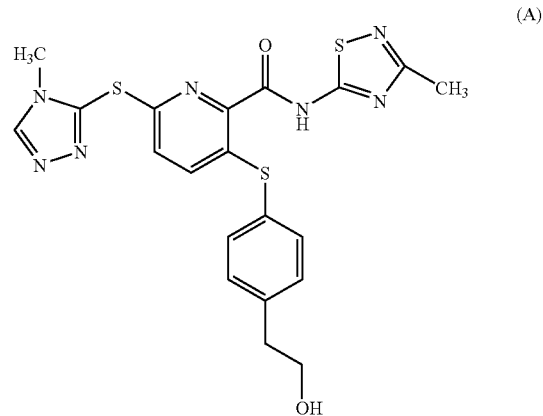

(A)

The compound of formula (A) is similar to the compounds of the present invention in that they have a methyl group at the 4-position of the triazole group and have a methyl group at the 3-position of the thiadiazole group therein, but the compounds of the present invention do not have a hydroxyalkyl group on the phenyl group therein.

Except the compound of formula (A), Patent Reference 1 discloses no concrete compounds having a methyl group at the 4-position of the triazole group and having a methyl group at the 3-position of the thiadiazole group therein.

Patent Reference 1: WO2004/081001
Non-Patent Reference 1:
Garfinkel D, et al., "Computer modeling identifies glucokinase as glucose sensor of pancreatic beta-cells", American Journal Physiology, Vol. 247 (3Pt2), 1984, pp. 527-536
Non-Patent Reference 2:
Grupe A. et al., "Transgenic knockouts reveal a critical requirement for pancreatic beta cell glucokinase in maintaining glucose homeostasis", Cell, Vol. 83, 1995, pp. 69-78
Non-Patent Reference 3:
Ferre T. et al., "Correction of diabetic alterations by glucokinase", Proceedings of the National Academy of Sciences of the U.S.A., Vol. 93, 1996, pp. 7225-7230
Non-Patent Reference 4:
Vionnet N. et al., "Nonsense mutation in the glucokinase gene causes early-onset non-insulin-dependent diabetes mellitus", Nature Genetics, Vol. 356, 1992, pp. 721-722
Non-Patent Reference 5:
Glaser B. et al., "Familial hyperinsulinism caused by an activating glucokinase mutation", New England Journal Medicine, Vol. 338, 1998, pp. 226-230

SUMMARY OF THE INVENTION

We, the present inventors have assiduously studied so as to provide a remedy and/or a preventive for diabetes, capable of binding to glucokinase to increase the activity of glucokinase, and to provide a anti-obesity agent having an action of stimulating a satiety center by activating glucokinase, and also to provide those compounds which have physical properties appropriate for drugs, and as a result have found that the compounds of formula (I) have a glucokinase-activating effect, and have an excellent solubility and/or pharmacological effect compared to known 2-pyridine carboxamide derivatives and have completed the present invention.

Specifically, the invention relates to a compound or its pharmaceutically-acceptable salt of a formula (I):

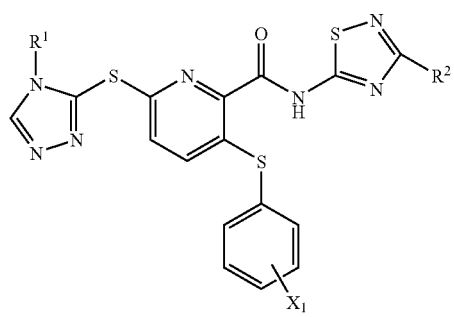

(I)

wherein:
$R^1$ and $R^2$ are each independently lower alkyl group;
$X^1$ represent a formula (II-1):

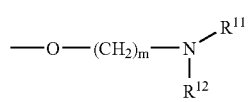

(II-1)

wherein:
$R^{11}$ and $R^{12}$ each independently a hydrogen atom or a lower alkyl group;

$R^{11}$, $R^{12}$ and a nitrogen atom together form a 4- to 7-membered nitrogenous aliphatic ring;
any one of carbon atoms in $(CH_2)_m$ and $R^{11}$ or $R^{12}$ together form a 4- to 7-membered aliphatic ring;
said 4- to 7-membered aliphatic ring being substituted with oxo group;
said a nitrogen atom to which both $R^{11}$ and $R^{12}$ bind being added with an oxygen atom;
said any one of carbon atoms in $(CH_2)m$ being substituted with lower alkyl group;
m represents an integer of 1 to 3;
or a formula (II-2):

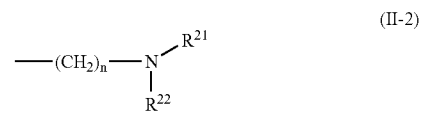

(II-2)

wherein:
$R^{21}$ and $R^{22}$ each independently represent hydrogen atom or lower alkyl group;
or $R^{21}$, $R^{22}$ and a nitrogen atom together may form a 4- to 7-membered aliphatic ring;
said 4- to 7-membered aliphatic ring being substituted with oxo group;
any one of the carbon atoms in $(CH_2)_n$ being substituted with lower alkyl group;
and n is an integer of 0 or 1.

The invention also relates to a pharmaceutical composition comprising the compounds of formula (I) or a pharmaceutically-acceptable salt thereof.

And the invention relates to remedies and/or preventives for diabetes or obesity.

The 2-pyridinecarboxamide derivatives and their pharmaceutically-acceptable salts of formula (I) of the invention have a strong glucokinase-activating effect, and are useful for treatment and/or prevention of diabetes, diabetes complications or obesity.

The compounds of the invention are applicable to diabetes of any type of insulin-dependent diabetes mellitus (IDDM) and non-insulin-dependent diabetes mellitus (NIDDM).

Diabetes complications as referred to herein are the disorders to be caused by diabetes. Concretely, the diabetes complications includes, for example, diabetic nephropathy, diabetic retinopathy, diabetic neurosis, and diabetic arteriosclerosis.

DESCRIPTION OF THE PREFERRED EMBODIMENTS

The meanings of the terms used in this description are described below, and the compounds of the invention are described in more detail hereinunder.

"Halogen atom" includes, for example, a fluorine atom, a chlorine atom, a bromine atom, an iodine atom.

"Lower alkyl group" means a linear or branched alkyl group having from 1 to 6 carbon atoms, including, for example, a methyl group, an ethyl group, a propyl group, an isopropyl group, a butyl group, an isobutyl group, a sec-butyl group, a tert-butyl group, a pentyl group, an isoamyl group, a neopentyl group, an isopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, a 1-ethyl-2-methylpropyl group.

"Alkoxy group" means a hydroxyl group of which the hydrogen atom is substituted with the above-mentioned lower alkyl group, and includes, for example, a methoxy group, an ethoxy group, a propoxy group, an isopropoxy group, a butoxy group, a sec-butoxy group, a tert-butoxy group, a pentyloxy group, an isopentyloxy group, a hexyloxy group, an isohexyloxy group.

For more concretely disclosing the compounds of formula (I) of the invention:

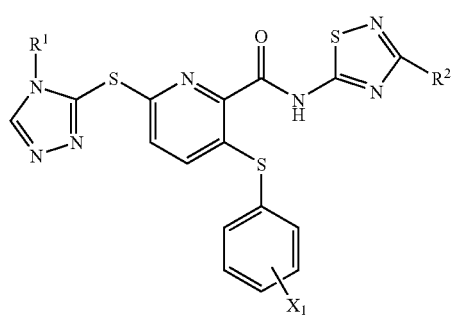

(I)

(wherein the symbols have the same meanings as above), the symbols used in formula (I) are described below with reference to their examples.

$R^1$ and $R^2$ each independently represent a lower alkyl group.

"Lower alkyl group" for $R^1$ and $R^2$ has the same meaning as the above-defined "lower alkyl group". Of those, preferably, $R^1$ and $R^2$ each independently represent a methyl group, an ethyl group, an n-propyl group or an isopropyl group, more preferably $R^1$ and $R^2$ each independently represent a methyl group or an ethyl group, even more preferably both $R^1$ and $R^2$ are methyl groups.

$X^1$ represents a group of a formula (II-1):

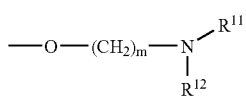

(II-1)

(wherein the symbols have the same meanings as above), or a group of a formula (II-2):

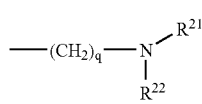

(II-2)

(wherein the symbols have the same meanings as above).

The group of formula (II-1) is described.

$R^{11}$ and $R^{12}$ each independently represent a hydrogen atom or a lower alkyl group.

"Lower alkyl group" for $R^{11}$ and $R^{12}$ has the same meaning as the above-defined "lower alkyl group". Concretely, it includes, for example, a methyl group, an ethyl group, an isopropyl group, an n-propyl group.

Concretely, the group of a formula:

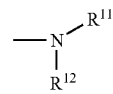

in which $R^{11}$ and $R^{12}$ each independently represent a hydrogen atom or a lower alkyl group, includes, for example, an amino group, a methylamino group, a dimethylamino group, an ethylamino group, a diethylamino group, an ethylmethylamino group.

When $R^{11}$ and $R^{12}$ each independently represent a hydrogen atom or a lower alkyl group, then an oxygen atom may be added to the nitrogen atom to which $R^{11}$ and $R^{12}$ bond.

Concretely, the group of a formula:

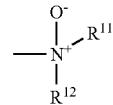

having an oxygen atom added thereto includes, for example, a dimethylnitroryl group, a diethylnitroryl group, an ethylmethylnitroryl group.

Taken together with the nitrogen atom to which they bond, $R^{11}$ and $R^{12}$ may form a 4- to 7-membered nitrogen-containing aliphatic ring, and one carbon atom to constitute the 4 to 7-membered nitrogen-containing aliphatic ring may be replaced by an oxygen atom.

Taken together with the nitrogen atom to which they bond, when $R^{11}$ and $R^{12}$ form a 4- to 7-membered nitrogen-containing aliphatic ring, they may bond to each other at any bondable position thereof.

One of $R^{11}$ pr $R^{12}$ may form, taken together with a carbon atom in $(CH_2)_m$ in formula (II-1), a 4- to 7-membered nitrogen-containing aliphatic ring.

Concretely, "4- to 7-membered nitrogen-containing aliphatic ring" in the case where, taken together with the nitrogen atom to which they bond, $R^{11}$ and $R^{12}$ form a 4- to 7-membered nitrogen-containing aliphatic ring (in which one carbon atom to constitute the ring may be replaced by an oxygen atom) includes, for example, an azetidin-1-yl group, a pyrrolidin-1-yl group, a (2R)-2-methylpyrrolidin-1-yl group, a (2S)-2-methylpyrrolidin-1-yl group, a piperidin-1-yl group, a hexamethyleneimin-1-yl group, a morpholin-4-yl group.

Concretely, the 4- to 7-membered nitrogen-containing aliphatic ring in the case where one of $R^{11}$ and $R^{12}$ forms, taken together with a carbon atom in $(CH_2)_m$ in formula (II-1), a 4- to 7-membered nitrogen-containing aliphatic ring includes, for example, a 1-methylazetidin-3-yl group, a 1-ethylazetidin-3-yl group, a 1-isopropylazetidin-3-yl group, a 1-isopropylpyrrolidin-3-yl group, a 1-methylpyrrolidin-2-yl group, a pyrrolidin-3-yl group, a 1-methylpyrrolidin-3-yl group, a 1-ethylpyrrolidin-3-yl group, a 1-methylpiperidin-4-yl group.

In the following group:

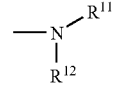

in formula (II-1), when $R^{11}$ and $R^{12}$ form, taken together with the nitrogen atom to which they bond, a 4- to 7-membered nitrogen-containing aliphatic ring; or in the following group:

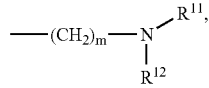

when $R^{11}$ and $R^{12}$ form, taken together with a carbon atom in $(CH_2)_m$, a 4- to 7-membered nitrogen-containing aliphatic ring, then the 4- to 7-membered nitrogen-containing aliphatic ring may be substituted with an oxo group, and an oxygen atom may be added to the nitrogen atom that constitutes the 4- to 7-membered nitrogen-containing aliphatic ring.

The 4- to 7-membered nitrogen-containing aliphatic ring substituted with an oxo group includes, for example, a 2-oxopyrrolidin-1-yl group, a 2-oxopiperidin-1-yl group, a 2-oxohexamethylenimin-1-yl group.

Concretely, the oxygen atom-added, 4- to 7-membered nitrogen-containing aliphatic ring is, for example, a 2-methyl-1-oxidopyrrolidin-1-yl group.

A carbon atom in $(CH_2)_m$ may be substituted with the above-defined lower alkyl group.

m indicates an integer of from 1 to 3.

From the above, the group of formula (II-1) concretely includes, for example, a 1-methylazetidin-3-yloxy group, a (1-ethylazetidin-3-yl)oxy group, a (1-isopropylazetidin-3-yl)oxy group, a 2-azetidin-1-ylethoxy group, a 2-pyrrolidin-1-ylethoxy group, a 2-(2-methylpyrrolidin-1-yl)ethoxy group, a 2-((2S)-methylpyrrolidin-1-yl)ethoxy group, a 2-((2R)-2-methylpyrrolidin-1-yl)ethoxy group, a pyrrolidin-3-yloxy group, a (3R)-pyrrolidin-3-yloxy group, a (1-methylpyrrolidin-2-yl)methoxy group, a ((2R)-1-methylpyrrolidin-2-yl)methoxy group, a ((2S)-1-methylpyrrolidin-2-yl)methoxy group, a (1-methylpyrrolidin-3-yl)methoxy group, a ((3S)-1-methylpyrrolidin-3-yl)methoxy group, a ((3S)-1-methylpyrrolidin-3-yl)methoxy group, a (1-methylpyrrolidin-3-yl)oxy group, a ((3S)-1-methylpyrrolidin-3-yl)oxy group, a ((3R)-1-methylpyrrolidin-3-yl)oxy group, a pyrrolidin-3-yloxy group, a (1-isopropylpyrrolidin-3-yl)oxy group, a 1-ethylpyrrolidin-3-yloxy group, a ((3R)-1-ethylpyrrolidin-3-yl)oxy group, a 2-(2-oxopyrrolidin-1-yl)ethoxy group, a (1-methylpiperidin-4-yl)oxy group, a 2-piperidin-1-ylethoxy group, a 2-(diethylamino)ethoxy group, a 2-(dimethylamino)ethoxy group, a 2-(ethylmethylamino)ethoxy group, a 2-(methylamino)ethoxy group, a 2-aminoethoxy group, a 3-pyrrolidin-1-ylpropoxy group, a 3-(dimethylamino)propoxy group, a 2-morpholin-4-ylethoxy group, a 2-(dimethylnitroryl)ethoxy group, a 2-(2-methyl-1-oxidopyrrolidin-1-yl)ethoxy group, a 2-((2R)-2-methyl-1-oxidopyrrolidin-1-yl)ethoxy group. Of those, preferred are a (1-ethylazetidin-3-yl)oxy group, a (1-isopropylazetidin-3-yl)oxy group, a 2-pyrrolidin-1-ylethoxy group, a 2-(2-methylpyrrolidin-1-yl)ethoxy group, a (1-methylpyrrolidin-3-yl)oxy group, a 2-(dimethylamino)ethoxy group.

The group of formula (II-2) is described.

$R^{21}$ and $R^{22}$ each independently represent a hydrogen atom or a lower alkyl group, or taken together with the nitrogen atom to which they bond, $R^{21}$ and $R^{22}$ may form a 4- to 7-membered nitrogen-containing aliphatic ring; and the 4- to 7-membered nitrogen-containing aliphatic ring may be substituted with an oxo group.

A carbon atom in $(CH_2)_n$ in formula (II-2) may be substituted with a lower alkyl group.

n indicates an integer of 0 or 1.

Concretely, the group of formula (II-2) includes, for example, a (2-oxopyrrolidin-1-yl)methyl group.

Of the compounds of formula (I), preferred are those of a formula (I-1):

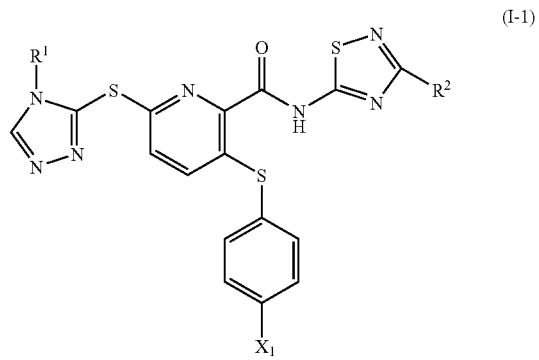

(wherein the symbols have the same meanings as above) or their pharmaceutically-acceptable salts; and more preferred are those of a formula (I-2):

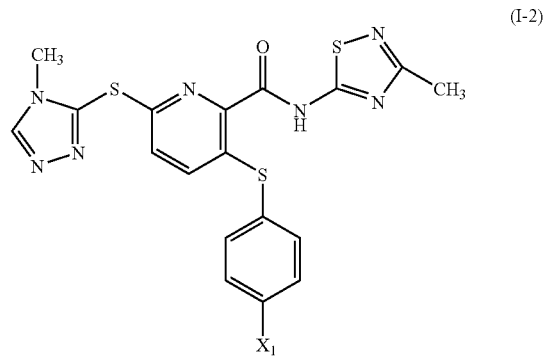

(wherein the symbols have the same meanings as above) or their pharmaceutically-acceptable salts.

Of $X_1$, preferred is a group of a formula (II-1):

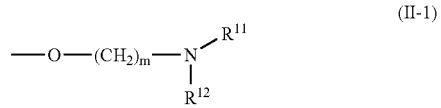

(wherein the symbols have the same meanings as above).

More preferred is dimethyl amino ethoxy group.

Preferred embodiments of $R^1$, $R^2$, $R^1$, $R^{12}$, $R^{21}$, $R^{22}$, $X_1$, m and n may be combined in any desired manner.

The solubility of the compounds of the present invention to water has greatly improved compared to the compounds disclosed in WO2004/081001, while maintaining the Glucokinase-activating activity and the The compounds of the present invention are suitable for pharmaceutical drugs.

Concretely, for example, the compounds of formula (I) include the following:

3-({4-[2-(dimethylamino)ethoxy]phenyl}thio)-N-(3-methyl-1,2,4-thiadiazol-5-yl)-6-[(4-methyl-4H-1,2,4-triazol-3-yl)thio]pyridine-2-carboxamide, 3-({4-[(1-methylazetidin-3-yl)oxy]phenyl}thio)-N-(3-methyl-1,2,4-thiadiazol-5-yl)-6-[(4-methyl-4H-1,2,4-triazol-3-yl)thio]pyridine-2-carboxamide, N-(3-methyl-1,2,4-thiadiazol-5-yl)-6-[(4-methyl-4H-1,2,4-triazol-3-yl)thio]-3-{[4-(2-pyrrolidin-1-ylethoxy)phenyl]thio}pyridine-2-carboxamide, 3-[(4-{2-[(2R)-2-methylpyrrolidin-1-yl]ethoxy}phenyl)thio-N-(3-methyl-1,2,4-thiadiazol-5-yl)-6-[(4-methyl-4H-1,2,4-triazol-3-yl)thio]pyridine-2-carboxamide, 3-[(4-{2-[(2S)-2-methylpyrrolidin-1-yl]ethoxy}phenyl)thio-N-(3-methyl-1,2,4-thiadiazol-5-yl)-6-[(4-methyl-4H-1,2,4-triazol-3-yl)thio]pyridine-2-carboxamide, 3-[(4-{[(2R)-1-methylpyrrolidin-2-yl]methoxy}phenyl)thio-N-(3-methyl-1,2,4-thiadiazol-5-yl)-6-[(4-methyl-4H-1,2,4-triazol-3-yl)thio]pyridine-2-carboxamide, 3-[(4-{[(2S)-1-methylpyrrolidin-2-yl]methoxy}phenyl)thio]-N-(3-methyl-1,2,4-thiadiazol-5-yl)-6-[(4-methyl-4H-1,2,4-triazol-3-yl)thio]pyridine-2-carboxamide, 3-{[4-(2-azetidin-1-ylethoxy)phenyl]thio}-N-(3-methyl-1,2,4-thiadiazol-5-yl)-6-[(4-methyl-4H-1,2,4-triazol-3-yl)thio]pyridine-2-carboxamide, 3-[(4-{[(3S)-1-methylpyrrolidin-3-yl]methoxy}phenyl)thio-N-(3-methyl-1,2,4-thiadiazol-5-yl)-6-[(4-methyl-4H-1,2,4-triazol-3-yl)thio]pyridine-2-carboxamide, 3-[(4-{[(3R)-1-methylpyrrolidin-3-yl]methoxy}phenyl)thio-N-(3-methyl-1,2,4-thiadiazol-5-yl)-6-[(4-methyl-4H-1,2,4-triazol-3-yl)thio]pyridine-2-carboxamide, 3-[(4-{[(3S)-1-methylpyrrolidin-3-yl]oxy}phenyl)thio-N-(3-methyl-1,2,4-thiadiazol-5-yl)-6-[(4-methyl-4H-1,2,4-triazol-3-yl)thio]pyridine-2-carboxamide, 3-[(4-{[(3R)-1-methylpyrrolidin-3-yl]oxy}phenyl)thio-N-(3-methyl-1,2,4-thiadiazol-5-yl)-6-[(4-methyl-4H-1,2,4-triazol-3-yl)thio]pyridine-2-carboxamide, 3-({4-[(1-methylpiperidin-4-yl)oxy]phenyl}thio)-N-(3-methyl-1,2,4-thiadiazol-5-yl)-6-[(4-methyl-4H-1,2,4-triazol-3-yl)thio]pyridine-2-carboxamide, N-(3-methyl-1,2,4-thiadiazol-5-yl)-6-[(4-methyl-4H-1,2,4-triazol-3-yl)thio]-3-{[4-(3-pyrrolidin-1-ylpropoxy)phenyl]thio}pyridine-2-carboxamide, 3-({4-[3-(dimethylamino)propoxy]phenyl}thio)-N-(3-methyl-1,2,4-thiadiazol-5-yl)-6-[(4-methyl-4H-1,2,4-triazol-3-yl)thio]pyridine-2-carboxamide, 3-({4-[2-(methylamino)ethoxy]phenyl}thio)-N-(3-methyl-1,2,4-thiadiazol-5-yl)-6-[(4-methyl-4H-1,2,4-triazol-3-yl)thio]pyridine-2-carboxamide, 3-{[4-(2-aminoethoxy)phenyl]thio}-N-(3-methyl-1,2,4-thiadiazol-5-yl)-6-[(4-methyl-4H-1,2,4-triazol-3-yl)thio]pyridine-2-carboxamide, N-(3-methyl-1,2,4-thiadiazol-5-yl)-6-[(4-methyl-4H-1,2,4-triazol-3-yl)thio]-3-({4-[(3R)-pyrrolidin-3-yloxy]phenyl}thio)pyridin-2-carboxamide, 3-({4-[(1-isopropylazetidin-3-yl)oxy]phenyl}thio)-N-(3-methyl-1,2,4-thiadiazol-5-yl)-6-[(4-methyl-4H-1,2,4-triazol-3-yl)thio]pyridine-2-carboxamide, 3-[(4-{[(3R)-1-isopropylpyrrolidin-3-yl]oxy}phenyl)thio]-N-(3-methyl-1,2,4-thiadiazol-5-yl)-6-[(4-methyl-4H-1,2,4-triazol-3-yl)thio]pyridine-2-carboxamide, N-(3-methyl-1,2,4-thiadiazol-5-yl)-6-[(4-methyl-4H-1,2,4-triazol-3-yl)thio]-3-({4-[(2-oxopyrrolidin-1-yl)methyl]phenyl}thio)pyridine-2-carboxamide, 3-({4-[2-(dimethylnitroryl)ethoxy]phenyl}thio)-N-(3-methyl-1,2,4-thiadiazol-5-yl)-6-[(4-methyl-4H-1,2,4-triazol-3-yl)thio]pyridine-2-carboxamide, 3-[(4-{2-[ethyl(methyl)amino]ethoxy}phenyl)thio]-N-(3-methyl-1,2,4-thiadiazol-5-yl)-6-[(4-methyl-4H-1,2,4-triazol-3-yl)thio]pyridine-2-carboxamide, 3-({4-[2-(diethylamino)ethoxy]phenyl}thio)-N-(3-methyl-1,2,4-thiadiazol-5-yl)-6-[(4-methyl-4H-1,2,4-triazol-3-yl)thio]pyridine-2-carboxamide, 3-({4-[(1-ethylazetidin-3-yl)oxy]phenyl}thio)-N-(3-methyl-1,2,4-thiadiazol-5-yl)-6-[(4-methyl-4H-1,2,4-triazol-3-yl)thio]pyridine-2-carboxamide, N-(3-methyl-1,2,4-thiadiazol-5-yl)-6-[(4-methyl-4H-1,2,4-triazol-3-yl)thio]-3-{[4-(2-piperidin-1-ylethoxy)phenyl]thio}pyridine-2-carboxamide, N-(3-methyl-1,2,4-thiadiazol-5-yl)-6-[(4-methyl-4H-1,2,4-triazol-3-yl)thio]-3-{[4-(2-morpholin-4-ylethoxy)phenyl]thio}pyridine-2-carboxamide, 3-[(4-{[(3R)-1-ethylpyrrolidin-3-yl]oxy}phenyl)thio]-N-(3-methyl-1,2,4-thiadiazol-5-yl)-6-[(4-methyl-4H-1,2,4-triazol-3-yl)thio]pyridine-2-carboxamide, N-(3-methyl-1,2,4-thiadiazol-5-yl)-6-[(4-methyl-4H-1,2,4-triazol-3-yl)thio]-3-({4-[2-(2-oxopyrrolidin-1-yl)ethoxy]phenyl}thio)pyridine-2-carboxamide or 3-[(4-{2-[(2R)-2-methyl-1-oxidopyrrolidin-1-yl]ethoxy}phenyl)thio]-N-(3-methyl-1,2,4-thiadiazol-5-yl)-6-[(4-methyl-4H-1,2,4-triazol-3-yl)thio]pyridine-2-carboxamide.

Among them, preferred compounds of the present invention are 3-({4-[2-(dimethylamino)ethoxy]phenyl}thio)-N-(3-methyl-1,2,4-thiadiazol-5-yl)-6-[(4-methyl-4H-1,2,4-triazol-3-yl)thio]pyridin-2-carboxamide, 3-[(4-{2-[ethyl(methyl)amino]ethoxy}phenyl)thio]-N-(3-methyl-1,2,4-thiadiazol-5-yl)-6-[(4-methyl-4H-1,2,4-triazol-3-yl)thio]pyridine-2-carboxamide, 3-({4-[2-(diethylamino)ethoxy]phenyl}thio)-N-(3-methyl-1,2,4-thiadiazol-5-yl)-6-[(4-methyl-4H-1,2,4-triazol-3-yl)thio]pyridine-2-carboxamide, 3-[(4-{2-[(2R)-2-methylpyrrolidin-1-yl]ethoxy}phenyl)thio-N-(3-methyl-1,2,4-thiadiazol-5-yl)-6-[(4-methyl-4H-1,2,4-triazol-3-yl)thio]pyridine-2-carboxamide, 3-[(4-{2-[(2S)-2-methylpyrrolidin-1-yl]ethoxy}phenyl)thio-N-(3-methyl-1,2,4-thiadiazol-5-yl)-6-[(4-methyl-4H-1,2,4-triazol-3-yl)thio]pyridine-2-carboxamide, 3-({4-[(1-ethylazetidin-3-yl)oxy]phenyl}thio)-N-(3-methyl-1,2,4-thiadiazol-5-yl)-6-[(4-methyl-4H-1,2,4-triazol-3-yl)thio]pyridine-2-carboxamide, 3-[(4-{[(3S)-1-methylpyrrolidin-3-yl]methoxy}phenyl)thio-N-(3-methyl-1,2,4-thiadiazol-5-yl)-6-[(4-methyl-4H-1,2,4-triazol-3-yl)thio]pyridine-2-carboxamide, 3-[(4-{[(3R)-1-methylpyrrolidin-3-yl]methoxy}phenyl)thio-N-(3-methyl-1,2,4-thiadiazol-5-yl)-6-[(4-methyl-4H-1,2,4-triazol-3-yl)thio]pyridine-2-carboxamide, 3-({4-[2-(methylamino)ethoxy]phenyl}thio)-N-(3-methyl-1,2,4-thiadiazol-5-yl)-6-[(4-methyl-4H-1,2,4-triazol-3-yl)thio]pyridine-2-carboxamide, or 3-{[4-(2-aminoethoxy)phenyl]thio}-N-(3-methyl-1,2,4-thiadiazol-5-yl)-6-[(4-methyl-4H-1,2,4-triazol-3-yl)thio]pyridine-2-carboxamide.

Methods for producing the compounds of the invention are described below.

The compounds of the following formula (I) of the invention can be produced, for example, according to the method mentioned below.

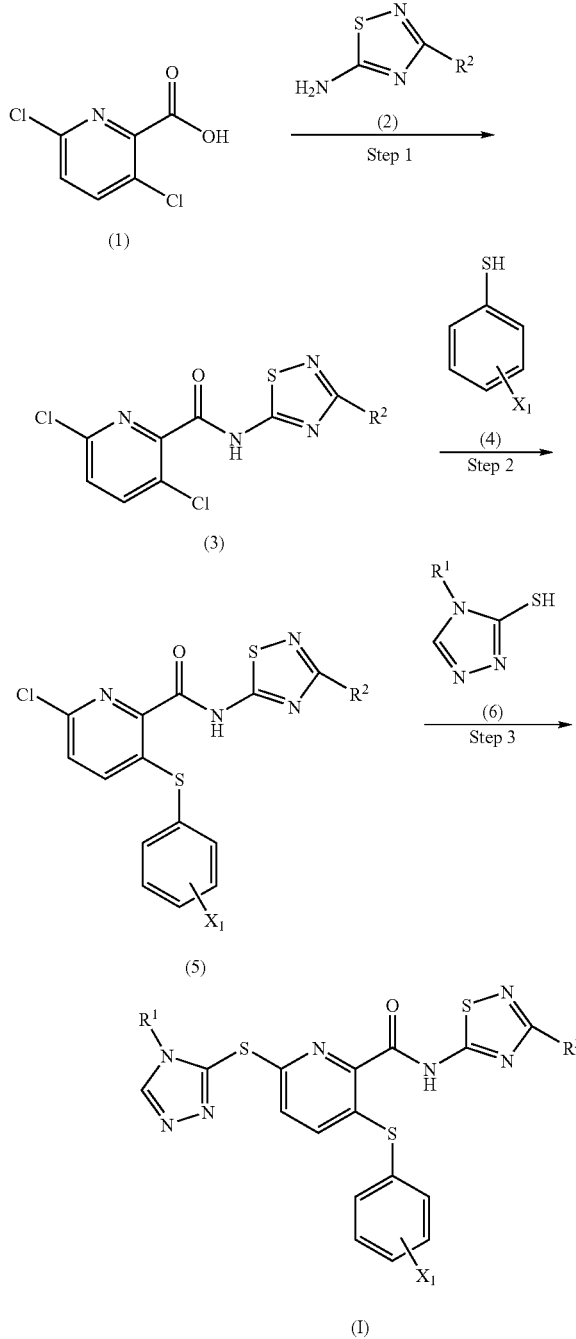

(wherein the symbols have the same meanings as above.)

Step 1:

This step is a method of reacting a dichloropyridinecarboxylic acid (1) or its reactive derivative with an amino compound (2) to produce a compound (3).

This reaction may be ordinary amidation to be attained according to a method described in references (e.g., Bases and Experiments of Peptide Synthesis, Nobuo Izumiya, et al., Maruzen, 1983; Comprehensive Organic Synthesis, Vol. 6, Pergamon Press, 1991), or according to a method is similar to it, or according to an ordinary method combined with it. Specifically, a condensing agent well known to those skilled in the art is used; or an ester activation method, a mixed acid anhydride method, an acid chloride method or a carbodiimide method available to those skilled in the art may be employed. The amidation reagent includes, for example, thionyl chloride, oxalyl chloride, N,N-dicyclohexylcarbodiimide, 1-methyl-2-bromopyridinium iodide, N,N'-carbonyldiimidazole, diphenylphosphoryl chloride, diphenylphosphoryl azide, N,N'-disuccinimidyl carbonate, N,N'-disuccinimidyl oxalate, 1-ethyl-3-(3-dimethylaminopropyl)carbodiimide hydrochloride, ethyl chloroformate, isobutyl chloroformate, benzotriazol-1-yl-oxy-tris(dimethylamino)phosphonium hexafluorophosphate. Of those, for example, preferred are thionyl chloride, 1-ethyl-3-(3-dimethylaminopropyl)carbodiimide hydrochloride, N,N-dicyclohexylcarbodiimide, benzotriazol-1-yl-oxy-tris(dimethylamino)phosphonium hexafluorophosphate. In the amidation, a base and a condensation promoter may be used along with the above amidation reagent.

The base to be used includes, for example, tertiary aliphatic amines such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU), 1,5-azabicyclo[4.3.0]non-5-ene (DBN); aromatic amines such as pyridine, 4-dimethylaminopyridine, picoline, lutidine, quinoline, isoquinoline. Of those, for example, preferred are tertiary aliphatic amines, and more preferred are, for example, triethylamine, N,N-diisopropylethylamine.

The condensation promoter to be used includes, for example, N-hydroxybenzotriazole hydrate, N-hydroxysuccinimide, N-hydroxy-5-norbornene-2,3-dicarboxylmide, 3-hydroxy-3,4-dihydro-4-oxo-1,2,3-benzotriazole. Of those, for example, preferred is N-hydroxybenzotriazole.

The compound (2) to be used concretely includes, for example, 5-amino-3-methyl-1,2,4-thiadiazole, 5-amino-3-ethyl-1,2,4-thiadiazole, 5-amino-3-propyl-1,2,4-thiadiazole.

The amount of the compound (2) to be used may vary, depending on the type of the compound and the solvent used and on the other reaction conditions, and, for example, it may be generally from 1 to 10 equivalents, preferably from 1 to 3 equivalents relative to 1 equivalent of the compound (1) or its reactive derivative.

The amount of the base to be used may also vary depending on the type of the compound and the solvent used and on the other reaction conditions, and, for example, it may be generally from 1 to 10 equivalents, preferably from 1 to 5 equivalents.

The reaction solvent to be used in this step is, for example, an inert solvent, which is not specifically defined so far as it does not interfere with the reaction. Concretely, for example, it includes methylene chloride, chloroform, 1,2-dichloroethane, dimethylformamide, ethyl acetate, methyl acetate, acetonitrile, benzene, xylene, toluene, 1,4-dioxane, tetrahydrofuran, dimethoxyethane, and their mixed solvents. For ensuring the preferred reaction temperature, for example, preferred are methylene chloride, chloroform, 1,2-dichloroethane, acetonitrile, N,N-dimethylformamide.

The reaction time may be generally from 0.5 to 96 hours, preferably from 3 to 24 hours.

The reaction time may be generally from 0° C. to the boiling temperature of the solvent, preferably from room temperature to 80° C.

The base, the amidation reagent and the condensation promoter to be used in this step may be one or more different types of compounds for them either singly or as combined.

The compound (3) thus obtained may be subjected to the next step, after isolated and purified in any known manner for separation and purification, for example, through concentration, concentration under reduced pressure, crystallization, solvent extraction, reprecipitation, chromatography, or not after isolated and purified.

Step 2:

This step is a method of reacting the compound (3) obtained in the above step 1 with a thiol compound (4) in the presence of a base to produce a compound (5).

Concretely, the thiol compound (4) to be used in this reaction includes, for example, 4-hydroxyphenol, 4-mercaptobenzoic acid, (4-mercaptophenyl)acetic acid, (4-mercaptophenyl)methanol.

The amount of the compound (4) to be used in this step may be generally from 0.2 to 20 equivalents, preferably from 1 to 10 equivalents relative to one equivalent of the compound (3).

Concretely, the base to be used in this step includes, for example, tertiary aliphatic amines such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU), 1,5-azabicyclo[4.3.0]non-5-ene (DBN); aromatic amines such as pyridine, 4-dimethylaminopyridine, picoline, lutidine, quinoline, isoquinoline; alkali metals such as potassium metal, sodium metal, lithium metal; alkali metal hydrides such as sodium hydride, potassium hydride; alkali metal alkylates such as butyllithium; alkali metal alkoxides such as potassium tert-butoxide, sodium ethoxide, sodium methoxide; alkali metal hydroxides such as potassium hydroxide, sodium hydroxide; alkali metal carbonates such as potassium carbonate, sodium carbonate, cesium carbonate. Of those, preferred are tertiary aliphatic amines, alkali metal hydrides, alkali metal carbonates and alkali metal alkoxides; and more preferred are, for example, sodium hydride, potassium carbonate, potassium tert-butoxide, sodium ethoxide, sodium methoxide.

The amount of the base to be used may be generally from 1 to 10 equivalents, preferably from 1 to 5 equivalents relative to one equivalent of the compound (3).

The reaction solvent to be used in this step is, for example, preferably an organic inert solvent, which is not specifically defined so far as it does not interfere with the reaction. Concretely, for example, it includes methylene chloride, chloroform, 1,2-dichloroethane, trichloroethane, dimethylformamide, dimethylacetamide, N-methylpyrrolidone, acetone, tert-butanol, tert-amyl alcohol, ethyl acetate, methyl acetate, acetonitrile, benzene, xylene, toluene, 1,4-dioxane, tetrahydrofuran, dimethoxyethane, and their mixed solvents. Preferred are dimethylformamide, dimethylacetamide, N-methylpyrrolidone, acetonitrile, tert-amyl alcohol; and more preferred are N,N-dimethylformamide, dimethylacetamide, N-methylpyrrolidone, acetonitrile.

The reaction time may be generally from 0.2 to 100 hours, preferably from 1 to 40 hours.

The reaction temperature may be generally from −20° C. to the boiling point of the solvent, preferably from 0° C. to the boiling point of the solvent.

The compound (5) thus obtained may be subjected to the next step, after isolated and purified in any known manner for separation and purification, for example, through concentration, concentration under reduced pressure, crystallization, solvent extraction, reprecipitation, chromatography, or not after isolated and purified.

Step 3:

This step is a method of reacting the compound (5) obtained in the above step 2 with a compound (6) in the presence of a base to produce a compound (I) of the invention.

Concretely, the compound (6) to be used in this step includes, for example, 4-methyl-4H-1,2,4-triazol-3-ylthiol, 4-ethyl-4H-1,2,4-triazol-3-ylthiol, 4-propyl-4H-1,2,4-triazol-3-ylthiol, 4-(1-methylethyl)-4H-1,2,4-triazol-3-ylthiol.

The amount of the compound (6) to be used may be generally from 0.2 to 20 equivalents, preferably from 1 to 10 equivalents relative to one equivalent of the compound (5).

The base to be used in this step may be the same as that used in the above step 2. Of those, preferred are potassium tert-butoxide and 1,8-diazabicyclo[5.4.0]undec-7-ene (DBU).

The amount of the base to be used may be generally from 0.2 to 10 equivalents, preferably from 1 to 5 equivalents relative to one equivalent of the compound (5).

The reaction solvent is, for example, preferably an inert organic solvent, which is not specifically defined so far as it does not interfere with the reaction. Concretely, for example, it includes methylene chloride, chloroform, 1,2-dichloroethane, trichloroethane, dimethylformamide, dimethylacetamide, N-methylpyrrolidone, acetone, ethanol, isopropanol, tert-butanol, tert-amyl alcohol, ethyl acetate, methyl acetate, acetonitrile, benzene, xylene, toluene, 1,4-dioxane, tetrahydrofuran, dimethoxyethane, and their mixed solvents. Of those, preferred are dimethylformamide, N-methylpyrrolidone, dimethylacetamide.

The reaction time may be generally from 0.2 to 100 hours, preferably from 1 to 40 hours.

The reaction temperature may be generally from 0° C. to the boiling point of the solvent, preferably from room temperature to the boiling point of the solvent.

The compound (1) of the invention thus obtained may be isolated and purified in any known manner for separation and purification, for example, through concentration, concentration under reduced pressure, crystallization, solvent extraction, reprecipitation, chromatography.

The compounds (1-2) of the invention can be produced, for example, according to the method mentioned below.

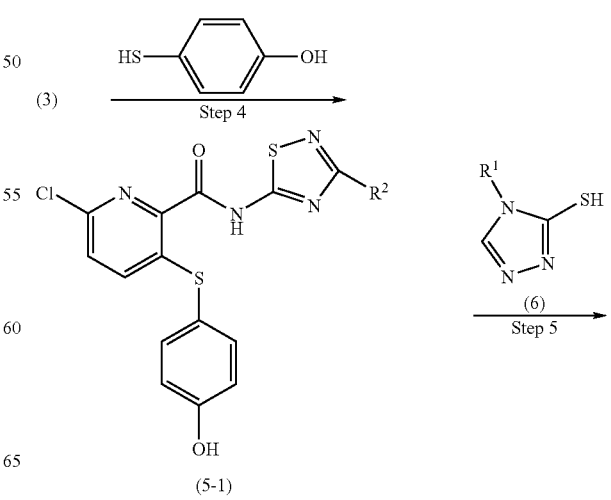

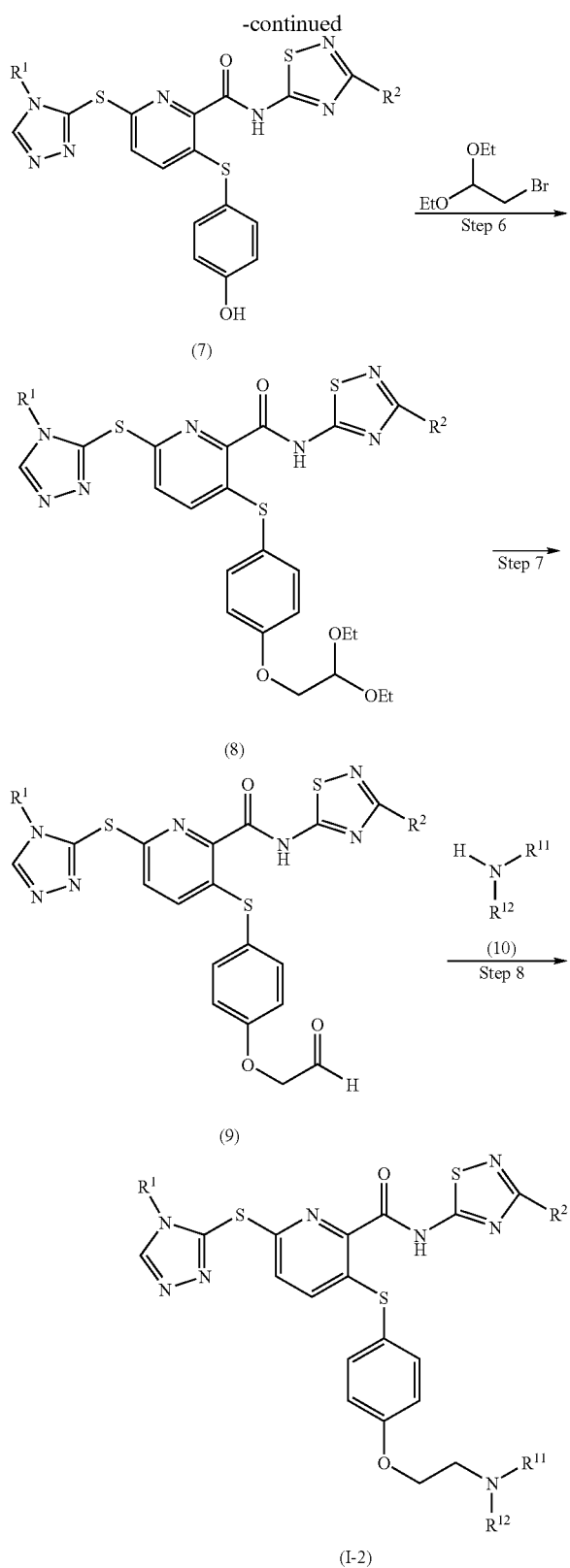

(wherein the symbols have the same meanings as above.)

Step 4:

This step is a method of reacting the compound (3) obtained in the above step 1 with 4-hydroxythiophenol in the presence of a base to produce a compound (5-1).

Concretely, the base to be used in this step includes, for example, trimethylamine, triethylamine, N,N-diisopropylethylamine, sodium hydride, potassium tert-butoxide, sodium ethoxide, sodium methoxide, potassium hydroxide, sodium hydroxide, potassium carbonate, sodium carbonate, cesium carbonate. Of those, preferred are sodium hydride, potassium tert-butoxide, cesium carbonate, potassium carbonate.

The base to be used may be generally from 0.2 to 10 equivalents, preferably from 1 to 5 equivalents relative to 1 equivalent of the compound (3).

The amount of 4-hydroxythiophenol to be used may be generally from 0.2 to 10 equivalents, preferably from 1 to 3 equivalents relative to one equivalent of the compound (3).

Not specifically defined, the reaction solvent to be used in this step may be any one not interfering with the reaction. For example, it includes methylene chloride, chloroform, 1,2-dichloroethane, trichloroethane, dimethylformamide, dimethylacetamide, N-methylpyrrolidone, acetone, ethanol, isopropanol, tert-butanol, tert-amyl alcohol, ethyl acetate, methyl acetate, acetonitrile, benzene, xylene, toluene, 1,4-dioxane, tetrahydrofuran, dimethoxyethane, and their mixed solvents. Of those, preferred are dimethylformamide, dimethylacetamide, N-methylpyrrolidone, acetonitrile, isopropanol, tert-amyl alcohol; and more preferred are N,N-dimethylformamide, dimethylacetamide, N-methylpyrrolidone, acetonitrile.

The reaction time may be generally from 0.2 to 100 hours, preferably from 1 to 40 hours.

The reaction temperature may be generally from 0° C. to the boiling point of the solvent, preferably from room temperature to the boiling point of the solvent.

The compound (5-1) thus obtained may be subjected to the next step, after isolated and purified in any known manner for separation and purification, for example, through concentration, concentration under reduced pressure, crystallization, solvent extraction, reprecipitation, chromatography, or not after isolated and purified.

Step 5:

This step is a method of reacting the compound (5-1) obtained in the above step 4 with a compound (6) in the presence of a base to produce a compound (7).

Concretely, the base to be used in this step includes, for example, trimethylamine, triethylamine, N,N-diisopropylethylamine, 1,8-diazabicyclo[5.4.0]undec-7-ene (DBU), 1,5-azabicyclo[4.3.0]non-5-ene (DBN), sodium hydride, potassium tert-butoxide, sodium ethoxide, sodium methoxide, potassium hydroxide, sodium hydroxide, potassium carbonate, sodium carbonate, cesium carbonate. Of those, preferred are 1,8-diazabicyclo[5.4.0]undec-7-ene (DBU), potassium tert-butoxide.

The amount of the base to be used may be generally from 0.2 to 10 equivalents, preferably from 1 to 5 equivalents relative to one equivalent of the compound (5-1).

The amount of the compound (6) to be used may be generally from 0.2 to 20 equivalents, preferably from 1 to 10 equivalents relative to one equivalent of the compound (5-1).

Not specifically defined, the reaction solvent to be used in this step may be any one not interfering with the reaction. For example, it includes methylene chloride, chloroform, 1,2-dichloroethane, trichloroethane, dimethylformamide, dimethylacetamide, N-methylpyrrolidone, acetone, ethanol, isopropanol, tert-butanol, tert-amyl alcohol, ethyl acetate, methyl acetate, acetonitrile, benzene, xylene, toluene, 1,4-dioxane, tetrahydrofuran, dimethoxyethane, and their mixed solvents. Of those, preferred are dimethylformamide, dimethylacetamide, N-methylpyrrolidone, acetonitrile, isopropanol, tert-amyl alcohol; and more preferred are dimethylformamide, dimethylacetamide, N-methylpyrrolidone, acetonitrile.

The reaction time may be generally from 0.2 to 100 hours, preferably from 1 to 40 hours.

The reaction temperature may be generally from −20° C. to the boiling point of the solvent, preferably from 0° C. to the boiling point of the solvent.

The compound (7) thus obtained may be subjected to the next step, after isolated and purified in any known manner for separation and purification, for example, through concentration, concentration under reduced pressure, crystallization, solvent extraction, reprecipitation, chromatography, or not after isolated and purified.

Step 6:

This step is a method of reacting the compound (7) obtained in the above step 5 with bromoacetaldehyde diethylacetal in the presence of a base to produce a compound (8).

Concretely, the base to be used in this step includes, for example, trimethylamine, triethylamine, N,N-diisopropylethylamine, sodium hydride, potassium tert-butoxide, sodium ethoxide, sodium methoxide, potassium hydroxide, sodium hydroxide, potassium carbonate, sodium carbonate, cesium carbonate. Of those, preferred are sodium hydride, potassium carbonate, cesium carbonate.

The amount of the base to be used may be generally from 0.2 to 10 equivalents, preferably from 1 to 5 equivalents relative to one equivalent of the compound (7).

The amount of bromoacetaldehyde diethylacetal to be used may be generally from 1 to 10 equivalents, preferably from 1 to 5 equivalents relative to one equivalent of the compound (7).

The reaction time may be generally from 0.2 to 100 hours, preferably from 1 to 40 hours.

The reaction temperature may be generally from −20° C. to the boiling point of the solvent, preferably from 0° C. to the boiling point of the solvent.

The compound (8) thus obtained may be subjected to the next step, after isolated and purified in any known manner for separation and purification, for example, through concentration, concentration under reduced pressure, crystallization, solvent extraction, reprecipitation, chromatography, or not after isolated and purified.

Step 7:

This step is a method of hydrolyzing the compound (8) obtained in the above step 6 with acid to produce a compound (9).

The acid to be used includes formic acid, hydrochloric acid, acetic acid, trifluoroacetic acid.

The amount of the acid to be used may be generally from 1 equivalent to a solvent amount, preferably from 1 to 100 equivalents.

The reaction time may be generally from 0.2 to 10 hours, preferably from 0.2 to 5 hours.

The reaction temperature may be generally from 0 to 60° C., preferably from 0° C. to room temperature.

The compound (9) thus obtained may be subjected to the next step, after isolated and purified in any known manner for separation and purification, for example, through concentration, concentration under reduced pressure, crystallization, solvent extraction, reprecipitation, chromatography, or not after isolated and purified.

Step 8:

This step is a method of reacting the compound (9) obtained in the above step 7 with a compound (10) in the presence of a reducing to produce a compound (I-2) of the invention.

The amount of the compound (10) to be used may be generally from 1 to 10 equivalents, preferably from 1 to 5 equivalents relative to one equivalent of the compound (9).

The reducing agent usable herein includes sodium triacetoxyborohydride, sodium cyanoborohydride.

The amount of the reducing agent to be used may be generally from 1 to 10 equivalents, preferably from 1 to 5 equivalents relative to one equivalent of the compound (9).

If desired, any of zinc chloride, acetic acid, trifluoroacetic acid, magnesium chloride or boron trifluoride may be added to this reaction system, and its amount may be generally from 1 to 10 equivalents, preferably from 1 to 3 equivalents relative to 1 equivalent of the compound (9).

Not specifically defined, the reaction solvent to be used in this step may be any one not interfering with the reaction. For example, it includes methanol, ethanol, acetic acid, tetrahydrofuran, chloroform, dichloromethane. Of those, preferred are chloroform, tetrahydrofuran, or methanol.

The reaction time may be generally from 1 to 24 hours, preferably from 1 to 8 hours.

The reaction temperature may be generally from 0° C. to 100° C., preferably from 0° C. to 40° C.

Step 9:

The compound (I-2) of the invention thus obtained may be isolated and purified in any known manner for separation and purification, for example, through concentration, concentration under reduced pressure, crystallization, solvent extraction, reprecipitation, chromatography.

The above compound (5) may be produced, for example, according to the method mentioned below.

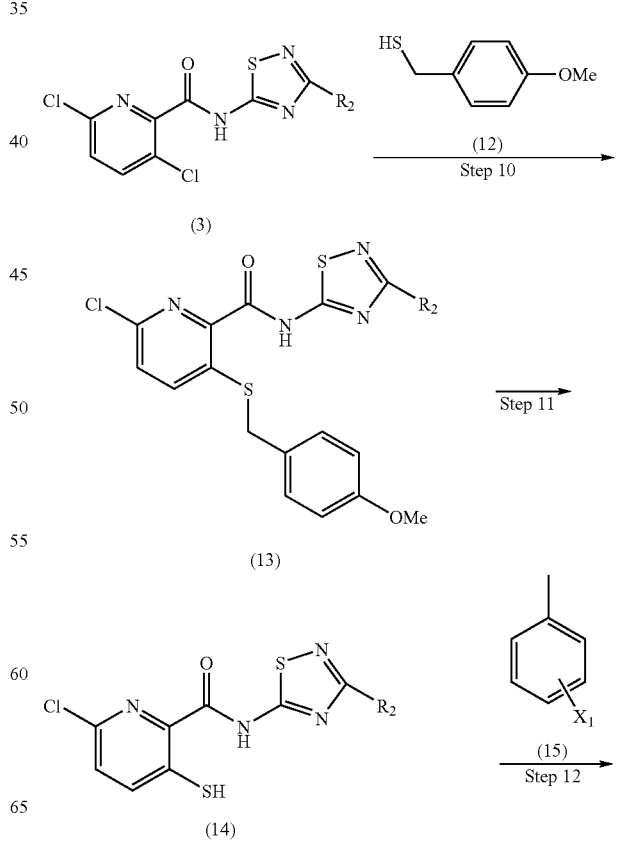

-continued

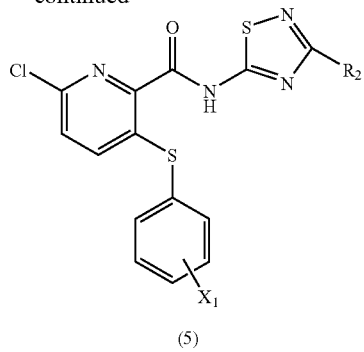

(5)

(wherein the symbols have the same meanings as above.)

Step 10:

This step is a method of reacting the compound (3) obtained in the above step 1 with (4-methoxyphenyl)methanethiol in the presence of a base to produce a compound (13).

Concretely, the base to be used in this step includes, for example, trimethylamine, triethylamine, N,N-diisopropylethylamine, 1,8-diazabicyclo[5.4.0]undec-7-ene (DBU), 1,5-azabicyclo[4.3.0]non-5-ene (DBN), sodium hydride, potassium tert-butoxide, sodium ethoxide, sodium methoxide, potassium hydroxide, sodium hydroxide, potassium carbonate, sodium carbonate, cesium carbonate. Of those, preferred are 1,8-diazabicyclo[5.4.0]undec-7-ene (DBU), potassium tert-butoxide.

The amount of the base to be used may be generally from 0.2 to 10 equivalents, preferably from 1 to 5 equivalents relative to one equivalent of the compound (3).

Not specifically defined, the reaction solvent to be used in this step may be any one not interfering with the reaction, but is, for example, preferably an inert organic solvent. Concretely, for example, it includes methylene chloride, chloroform, 1,2-dichloroethane, trichloroethane, dimethylformamide, dimethylacetamide, N-methylpyrrolidone, acetone, ethanol, isopropanol, tert-butanol, tert-amyl alcohol, ethyl acetate, methyl acetate, acetonitrile, benzene, xylene, toluene, 1,4-dioxane, tetrahydrofuran, dimethoxyethane, and their mixed solvents. Of those, preferred are dimethylformamide, N-methylpyrrolidone, dimethylacetamide.

The reaction time may be generally from 0.2 to 100 hours, preferably from 1 to 40 hours.

The reaction temperature may be generally from 0° C. to the boiling point of the solvent, preferably from room temperature to the boiling point of the solvent.

The compound (13) thus obtained may be subjected to the next step, after isolated and purified in any known manner for separation and purification, for example, through concentration, concentration under reduced pressure, crystallization, solvent extraction, reprecipitation, chromatography, or not after isolated and purified.

Step 11:

This step is a method of removing the thiol-protective group from the compound (13) obtained in the above step 10, with an acid to produce a compound (14).

Concretely, the acid to be used in this step includes, for example, trifluoroacetic acid, hydrochloric acid.

The amount of the acid to be used may be from 1 equivalent to a solvent amount for the compound (13).

Not specifically defined, the reaction solvent to be used in this step may be any one not interfering with the reaction. Concretely, for example, it includes tetrahydrofuran, 1,4-dioxane, chloroform. Of those, preferred are 1,4-dioxane, chloroform. When trifluoroacetic acid is used for the acid, then trifluoroacetic acid may serve both as the acid and as the solvent.

The reaction time may be generally from 0.2 to 10 hours, preferably from 1 to 5 hours.

The reaction temperature may be generally from 0° C. to 100° C., preferably from room temperature to 80° C.

The compound (14) thus obtained may be subjected to the next step, after isolated and purified in any known manner for separation and purification, for example, through concentration, concentration under reduced pressure, crystallization, solvent extraction, reprecipitation, chromatography, or not after isolated and purified.

Step 12:

This step is a method of reacting the compound (14) obtained in the above step 11 with a compound (15) in the presence of a base to produce a compound (5).

Concretely, the base to be used in this step includes, for example, trimethylamine, triethylamine, N,N-diisopropylethylamine, sodium hydride, potassium tert-butoxide, sodium ethoxide, sodium methoxide, potassium hydroxide, sodium hydroxide, potassium carbonate, sodium carbonate, cesium carbonate. Of those, preferred are sodium hydride, potassium carbonate, cesium carbonate.

The amount of the base to be used may be generally from 0.2 to 10 equivalents, preferably from 1 to 5 equivalents relative to one equivalent of the compound (14).

The compound (15) to be used concretely includes, for example, 4-iodoacetophenone, 1-iodo-4-(methoxymethyl)benzene.

Copper iodide may be added to the reaction system, and the amount of copper iodide may be generally from 0.01 to 5 equivalents, preferably from 0.1 to 2 equivalents relative to one equivalent of the compound (14).

Not specifically defined, the reaction solvent to be used in this step may be any one not interfering with the reaction. For example, it includes methylene chloride, chloroform, 1,2-dichloroethane, trichloroethane, dimethylformamide, dimethylacetamide, N-methylpyrrolidone, acetone, ethanol, isopropanol, tert-butanol, tert-amyl alcohol, ethyl acetate, methyl acetate, acetonitrile, benzene, xylene, toluene, 1,4-dioxane, tetrahydrofuran, dimethoxyethane, and their mixed solvents. Of those, preferred are dimethylformamide, dimethylacetamide, N-methylpyrrolidone, acetonitrile, isopropanol, tert-amyl alcohol; and more preferred are dimethylformamide, dimethylacetamide, N-methylpyrrolidone, acetonitrile.

The reaction time may be generally from 1 to 8 hours, preferably from 1 to 24 hours.

The reaction temperature may be generally from 0° C. to 150° C., preferably from 0° C. to 100° C.

The compound (5) thus obtained may be used as the starting compound in the above step 3 to produce the compound (I) of the invention, after isolated and purified in any known manner for separation and purification, for example, through concentration, concentration under reduced pressure, crystallization, solvent extraction, reprecipitation, chromatography, or not after isolated and purified.

In the reactions mentioned above, when $X_1$ has a protective group, then the protective group may be removed according to a method described in references (e.g., Protective Groups in Organic Synthesis, by T. W. Green, 2nd Ed., John Wiley & Sons, 1991), or according to a method is similar to it, or according to an ordinary method combined with it, thereby converting the protected compound into the compound of the invention.

The 2-pyridinecarboxamide derivatives that the invention provides may be in the form of their pharmaceutically-acceptable salts. The salts may be produced in any ordinary method from the compounds of the above formulae (I-1), (I-2) and (I-3) that are within the scope of the compounds (I) of the invention.

Concretely, when the compounds of formula (I), (I-1), (I-2) of (I-3) have a basic group derived from, for example, an amino group or a pyridyl group in the molecule, then the compounds may be processed with acid so as to convert them into the corresponding pharmaceutically-acceptable salts.

The acid-addition salts include, for example, hydrohalides such as hydrochlorides, hydrofluorides, hydrobromides, hydroiodides; inorganic acid salts such as nitrates, perchlorates, sulfates, phosphates, carbonates; lower alkylsulfonates such as methanesulfonates, trifluoromethanesulfonates, ethanesulfonates; arylsulfonates such as benzenesulfonates, p-toluenesulfonates; organic acid salts such as fumarates, succinates, citrates, tartrates, oxalates, maleates; other organic acid-addition salts with amino acid such as glutamates, aspartates. When the compounds of the invention have an acid group in the molecule, for example, when they have a carboxyl group, then the compounds may be processed with a base so as to convert them into the corresponding pharmaceutically-acceptable salts. The base-addition salts include, for example, alkali metal salts with sodium or potassium; alkaline earth metal salts with calcium or magnesium; ammonium salts; organic base-addition salts with guanidine, triethylamine, dicyclohexylamine, etc. In addition, the compounds of the invention may also be in any other form of hydrates or solvates of their free compounds or their salts.

Depending on the type of the substituents therein, the compounds of the invention include stereoisomers and tautomers such as optical isomers, diastereomeric isomers and geometrical isomers. Needless-to-say, the compounds of the invention include all these isomers. Further needless-to-say, the compounds of the invention include all mixtures of such isomers.

In producing medicines for prevention and remedy of type II diabetes or diseases or symptoms associated with it, the compounds of formula (I) of the invention may be combined with carrier substances for the use.

The dose of the compounds of formula (I) of the invention for prevention or remedy of diseases naturally varies, depending on the property of the symptom to be treated, the specific compound selected for it and the administration route.

In addition, the dose also varies depending on the age, the body weight and the sensitivity of patients. In general, the daily dose for one-time or plural-times administration may be from about 0.001 mg/kg-body weight to about 100 mg/kg-body weight, preferably from about 0.01 mg/kg-body weight to about 50 mg/kg-body weight, even more preferably from about 0.1 mg/kg-body weight to about 10 mg/kg-body weight. As the case may be, administration of a dose over the range may be necessary.

An example of a suitable dose for oral administration is described. The daily dose for one-time or two- to four-times administration may be at least from about 0.01 mg to at most 2.0 g. Preferably, the daily administration frequency is once or twice a day, and the daily dose is from about 1.0 mg to about 200 mg. More preferably, the daily dose is from about 10 mg to 100 mg for one-time administration a day.

For intravenous administration or oral administration, a typical dose of the compound (I) may be from about 0.001 mg/day/kg-body weight to about 100 mg/day/kg-body weight (preferably from 0.01 mg/day/kg-body weight to about 10 mg/day/kg-body weight), more preferably from about 0.1 mg/day/kg-body weight to 10 mg/day/kg-body weight.

As so mentioned hereinabove, the pharmaceutical composition of the invention comprises a compound of formula (I) and a pharmaceutically-acceptable carrier. The term "composition" is meant to contain not only a product produced by directly or indirectly combining, hybridizing or aggregating 2 or more ingredients, a product produced as a result of dissociation of one or more ingredients, or a compound produced as a result of reaction or interaction of different types of ingredients, but also an active and inactive ingredient of constituting a carrier (pharmaceutically-acceptable vehicle).

As combined with a pharmaceutically-acceptable carrier, the composition of the invention preferably contains a compound of formula (I) in an amount effective for remedy and prevention of type II diabetes and for retardation of the onset of the disease.

For administering the effective dose of the compound of the invention to mammals, especially to humans, employable is any suitable administration route. For example, the route may be oral administration, rectal administration, local administration, intravenous administration, ophthalmic administration, lung administration or nasal administration. Examples of the administration forms are tablets, troches, powders, suspensions, solutions, capsules, creams, aerosols. Preferred are oral tablets.

In preparing oral compositions, usable are any ordinary pharmaceutical media. Their examples are water, glycol, oil, alcohol, fragrant additives, preservatives, colorants. In preparing liquid compositions for oral administration, for example, mentioned are suspensions, elixirs and solutions. Their carriers are, for example, starch, sugar, microcrystalline cellulose, diluent, granulating promoter, lubricant, binder, disintegrator. In preparing solid compositions for oral administration, for example, mentioned are powders, capsules and tablets. Above all, such solid compositions for oral administration are preferred.

In view of the easiness in their administration, tablets and capsules are the most advantageous forms for oral administration. If desired, the tablets may be coated according to standard aqueous or non-aqueous coating techniques.

In addition to the above-mentioned ordinary administration modes for them, the compounds of formula (I) may also be administered according to controlled release systems and/or controlled delivery systems, for example, as in U.S. Pat. Nos. 3,845,770, 3,916,899, 3,536,809, 3,598,123, 3,630,200 and 4,008,719.

The pharmaceutical composition of the invention suitable for oral administration includes capsules, cashews and tablets that contain a predetermined amount of the active ingredient in the form of powders or granules thereof, or in the form of water-soluble liquids, water-insoluble liquids, oil-in-water emulsions or water-in-oil emulsions thereof. These compositions may be prepared in any pharmaceutical methods, and all the methods include a process of combining the active ingredient with a carrier of one or more necessary ingredients.

In general, the active ingredient is uniformly and fully mixed with a liquid carrier, or a well-separated solid carrier or with both the two, and then, if desired, the product is shaped into suitable forms to prepare the composition. For example, tablets are produced through compression and shaping, optionally along with one or more side components. Using a suitable machine, compressed tablets may be produced by mixing the active ingredient optionally with binder, lubricant, inert vehicle, surfactant or dispersant and compressing the resulting mix in any desired manner into powders or granules.

Shaped tablets may be prepared by shaping a mixture of a powdery wet compound and an inert liquid diluent, using a suitable machine.

Preferably, the tablets each contain from about 1 mg to 1 g of the active ingredient; and the cashews and the capsules each contain from about 1 mg to 500 mg of the active ingredient.

Examples of the administration modes of the compounds of formula (I) for pharmaceutical use are as follows:

TABLE 1

| Suspension for Injection (I. M.) | mg/ml |
|---|---|
| compound of formula (I) | 10 |
| methyl cellulose | 5.0 |
| Tween 80 | 0.5 |
| benzyl alcohol | 9.0 |
| benzalkonium chloride | 1.0 | water for injection is added to make 1.0 ml.

TABLE 2

| Tablets | mg/tablet |
|---|---|
| compound of formula (I) | 25 |
| methyl cellulose | 415 |
| Tween 80 | 14.0 |
| benzyl alcohol | 43.5 |
| magnesium stearate | 2.5 |
| total | 500 mg |

TABLE 3

| Capsules | mg/capsule |
|---|---|
| compound of formula (I) | 25 |
| lactose powder | 573.5 |
| magnesium stearate | 1.5 |
| total | 600 mg |

TABLE 4

| Aerosol | per one container |
|---|---|
| compound of formula (I) | 24 mg |
| lecithin, NF Liq. Conc. | 1.2 mg |
| trichlorofluoromethane, NF | 4.025 g |
| dichlorodifluoromethane, NF | 12.15 g |

The compounds of formula (I) may be used, as combined with any other medicines usable not only for type II diabetes-associated diseases or symptoms but also for remedy/prevention/retardation of the onset of type II diabetes. The additional medicines may be administered in any administration route and dose generally employed in the art, simultaneously with or separately from the compound of formula (I).

In case where the compound of formula (I) is used along with one or more other medicines, then a pharmaceutical composition comprising the compound of formula (I) and the additional medicines is preferred. Accordingly, the pharmaceutical composition of the invention may comprise not only the compound of formula (I) but also one or more such active ingredients. Examples of the active ingredients that may be combined with the compounds of formula (I) are mentioned below, which, however, are not limitative. These may be separately administered or may be administered simultaneously as contained in the same pharmaceutical composition.

(a) other glucokinase activators,
(b) bis-guanides (e.g., buformin, metoformin, fenformin,),
(c) PPAR agonists (e.g., triglytazon, pioglytazon, nosiglytazon),
(d) insulin,
(e) somatostatin,
(f) α-glucosidase inhibitors (e.g., boglybose, miglytol, acarbose),
(g) insulin secretion promoters (e.g., acetohexamide, calbutamide, chlorpropamide, glybomlide, glycrazide, glymerpide, glypidide, glyquidine, glysoxepide, glyburide, glyhexamide, glypinamide, fenbutamide, trazamide, tolbutamide, tolcyclamide, nateglynide, repaglynide), and
(h) DPP-IV (dipeptidyl peptidase IV) inhibitors).

The weight ratio of the compound of formula (I) to the second active ingredient may vary within a broad range, and depends on the effective amount of the individual active ingredients. Accordingly, for example, when the compound of formula (I) is combined with a PPAR agonist, then the weight ratio of the compound of formula (I) to the PPAR agonist may be generally from about 1000/1 to 1/1000, preferably from about 200/1 to 1/200. The combination of the compound of formula (D) and the other active ingredient may be within the above-mentioned range. In any case, an effective amount of the individual ingredients should be in the combination.

The glucokinase-activating potency of the compounds of formula (I) of the invention and the blood glucose-depressing potency thereof based on it may be confirmed, for example, according to the pharmaceutical experiments mentioned below.

Pharmacological Experiment 1 (Glucokinase-Activating Effect)

The glucokinase-activating potency of the compounds of formula (I) of the invention and a test method for it are described below.

The excellent glucokinase-activating effect of the compounds of formula (I) may be determined by a method described in references (for example, Diabetes, Vol. 45, pp. 1671-1677, 1996), or in accordance with it.

The glucokinase activity may be determined not by directly measuring glucose-6-phosphate but by measuring the level of Thio-NADH, which is produced when a reporter enzyme, glucose-6-phosphate dehydrogenase produces phosphogluconolactone from glucose-6-phosphate, and based on the level, the degree of glucokinase activation by the compound tested may be determined.

In this assay, used was a recombinant human liver GK, which was expressed by $E.\ coli$ as a FLAG fusion protein therein and was purified by ANTIFLAG M2 AFFINITY GEL (Sigma).

Using a flat-bottomed 96-well plate, the assay was carried out at 30° C. 69 μl of an assay buffer (25 mM Hepes Buffer/pH=7.2, 2 mM $MgCl_2$, 1 mM ATP, 0.5 mM TNAD, 1 mM dithiothreitol) was put into the plate, and 1 μl of a DMSO solution of the compound or DMSO alone as a control was added thereto. Next, 20 μl of an enzyme mixture (FLAG-GK, 20 U/ml G6PDH) cooled in ice was added to it, and 10 μl of a substrate, 25 mM glucose was added to it, and the reaction was initiated (final glucose concentration=2.5 mM).

After the start of the reaction, the increase in the absorbance at 405 nm was measured for 12 minutes at intervals of 30 seconds, and the increase for the first 5 minutes was used for assessing the compound tested. FLAG-GK was added so that the absorbance increase after 5 minutes in the presence of 1% DMSO could be from 0.04 to 0.06.

The OD level of the DMSO control was set as 100%; and the OD level of the test compound at different concentrations was determined. From the OD level at each concentration, Emax (%) and EC50 (μM) were computed and used as the index of the GK-activating potency of the compound.

The GK-activating potency of the compounds of the invention was measured according to the method as above, and the results are shown in Table 5 below.

TABLE 5

| Compound No. | Emax (%) | EC50 (μM) |
|---|---|---|
| Example 1 | 1105 | 0.09 |
| Example 4 | 1263 | 0.15 |
| Example 7 | 1210 | 0.06 |
| Example 20 | 964 | 0.04 |
| Example 23 | 1086 | 0.06 |
| Example 24 | 1074 | 0.04 |
| Example 25 | 1212 | 0.05 |
| Example 26 | 1219 | 0.07 |

Accordingly, the compounds of the invention have an excellent GK-activating potency indicated by Emax and EC50, as in the above Table.

The blood glucose-depressing potency of the compounds of the invention and a test method for it are described below.

Pharmacological Experiment 2 (Pharmacological Test in Dog)

Male beagle dogs (BW 9.6-13.8 kg) were fasted overnight. Pre-dose blood sampling was performed from cephalic vein. The test drugs, which were suspended into 0.5% methylcellulose, were orally administered (example 1 at 0.25, 0.5 and 1 mg/kg, and example 4, and compound B at 1 mg/kg). Control group was given 0.5% methylcellulose alone. Blood was taken every 0.5 or 1 hour after the drug dosing. Plasma sample were obtained by centrifugation, and the plasma glucose levels were measured by "Determiner GL-E" (Kyowa Medex Co., Ltd. Japan).

TABLE 6

| | | % Reduction of plasma glucose AUC for 4 hr after oral administration |
|---|---|---|
| Compounds | Dose (mg/kg) | % Reduction of plasma glucose AUC |
| Example 1 | 0.25 | 7.9 |
| | 0.5 | 10.6 |
| | 1 | 15.7 |
| Example 4 | 1 | 26.8 |
| Example 25 | 1 | 42.1 |
| Compound (B) | 1 | 7.4 |

The compound (B) used in comparison of the compounds of the present invention represents the formula:

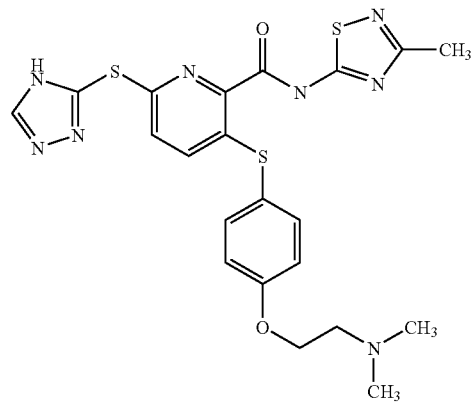

which is disclosed in WO2004/081001.

As in the above Table, the compounds of the invention have an excellent pharmacological effect.

Experiment 3 (Comparative Test of Solubility)

1 mg of compounds were placed in 1 ml of medium (JP-1, 200M potassium phosphate buffer) and was shaken on a shaking-incubator for 75 min. (1000 rpm). After centrifugation, concentration of supernatant was analyzed by HPLC.

JP1: pH1.2 (artificial gastric fluid: 35 mM NaCl, 84 mM HCl in water)

2.0 g of NaCl, 7.0 ml of HCl and water were mixed in a measuring flask (1000 ml).

200 mM potassium phosphate buffer: pH7.4

200 mM $K_2HPO_4$ and 200 mM $KH_2PO_4$ were mixed and adjusted to pH7.4 by using pH meter.

The results of the solubility of compound (A) and the compounds of example 1, 4, 7, 20, 23, 24, 25 and 26 are shown below.

TABLE 7

| | soulubility (μg/ml) | | |
|---|---|---|---|
| Compounds | Solubility to JP-1 | Solibility to 200 mM potassium phosphate buffer | Solubility to water |
| Compound (A) | 6.2 | 3.4 | 2.4 |
| Example 1 | >1000 | 17.5 | 15.2 |
| Example 4 | >1000 | 47.3 | 47.4 |
| Example 7 | >1000 | 307.8 | 582.9 |
| Example 20 | >1000 | 86.8 | 126.9 |
| Example 23 | >1000 | 122.4 | 208.1 |
| Example 24 | >1000 | 298.2 | 230.3 |
| Example 25 | >1000 | 13.8 | 16.4 |
| Example 26 | >1000 | 239.4 | 175.6 |

The compound (A) used in comparison of the compounds of the present invention represents the formula:

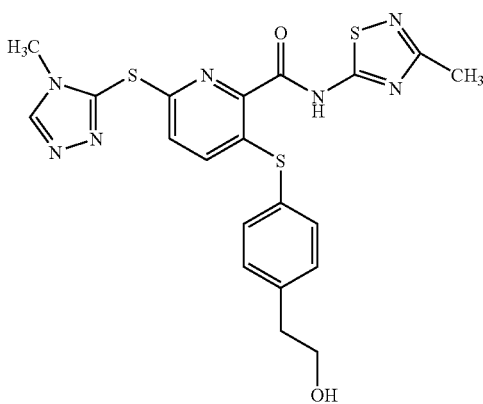

which is disclosed in WO2004/081001.

As in the above Table, the solubility of the compounds of the present invention are greatly improved and useful for drug.

EXAMPLES

The invention is described more concretely with reference to the following Preparation Examples, Examples and Reference Examples, by which, However, the Invention should not be limited at all.

Preparation Example 1

10 parts of the compound of Example 1, 15 parts of heavy magnesium oxide and 75 parts of lactose are uniformly mixed to give a powdery or particulate preparation of at most 350 μm in size. The preparation is encapsulated to prepare capsules.

Preparation Example 2

45 parts of the compound of Example 1, 15 parts of starch, 16 parts of lactose, 21 parts of crystalline cellulose, 3 parts of polyvinyl alcohol and 30 parts of distilled water are uniformly mixed, then ground, granulated and dried, and thereafter sieved to prepare granules having a size of from 1410 to 177 μm in diameter.

Preparation Example 3

Granules are prepared in the same manner as in Preparation Example 2. 3 parts of calcium stearate is added to 96 parts of the granules, and shaped under compression to give tablets having a diameter of 10 mm.

Preparation Example 4

10 parts of crystalline cellulose and 3 parts of calcium stearate are added to 90 parts of the granules obtained according to the method of Preparation Example 2, and shaped under compression to give tablets having a diameter of 8 mm. These are coated with a mixture suspension of syrup gelatin and precipitated calcium carbonate to prepare sugar-coated tablets.

In the thin-layer chromatography in Examples, Silicagel 60F$_{245}$ (Merck) was used for the plate, and a UV detector was used for detection. For the column silica gel, used was Wakogel™ C-300 (Wako Pure Chemical); and for the reversed-phase column silica gel, used was LC-SORB™ SP-B-ODS (Chemco) or YMC-GEL™ ODS-AQ 120-S50 (Yamamura Chemical Laboratory).

The meanings of the abbreviations in the following Examples are shown below.
i-Bu: isobutyl group
n-Bu: n-butyl group
t-Bu: t-butyl group
Me: methyl group
Et: ethyl group
Ph: phenyl group
i-Pr: isopropyl group
n-Pr: n-propyl group
CDCl$_3$: heavy chloroform
CD$_3$OD: heavy methanol
DMSO-d$_6$: heavy dimethylsulfoxide The meanings of the abbreviations in the following nuclear magnetic resonance spectra are shown below.
s: singlet
d: doublet
dd: double-doublet
t: triplet
m: multiplet
br: broad
brs: broad singlet
q: quartet
J: coupling constant
Hz: hertz

Reference Example

Production of 3-[(4-hydroxyphenyl)thio]-N-(3-methyl-1,2,4-thiadiazol-5-yl)-6-[(4-methyl-4H-1,2,4-triazol-3-yl)thio]pyridine-2-carboxamide

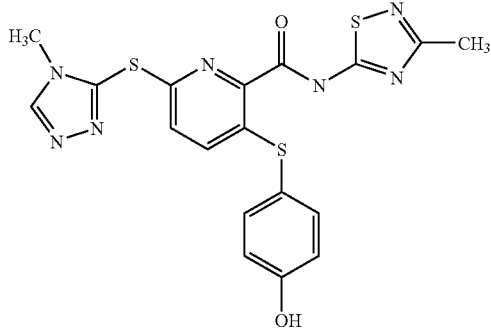

Step 1

Production of 3,6-dichloro-N-(3-methyl-1,2,4-thiadiazol-5-yl)pyridine-2-carboxamide 12 g of 5-amino-3-methyl-1,2,4-thiadiazole, 21.1 g of N-hydroxybenzotriazole hydrate and 29.8 g of 1-(3-dimethylaminopropyl)-3-ethylcarbodiimide hydrochloride were added to a chloroform (500 ml) solution of 21 g of 3,6-dichloro-2-pyridinecarboxylic acid, and stirred at room temperature for 1 hour and then stirred overnight at 50° C. The reaction liquid was diluted with chloroform, then washed with aqueous 0.2 N hydrochloric acid solution, water and saturated saline water. After this was dried with anhydrous magnesium sulfate, the solvent was evaporated away under reduced pressure, and ethyl acetate was added to the resulting residue for crystallization to obtain 22.7 g of the entitled compound as a white solid.

Step 2

Production of 6-chloro-3-[(4-hydroxyphenyl)thio]-N-(3-methyl-1,2,4-thiadiazol-5-yl)pyridine-2-carboxamide 12 g of 4-hydroxythiophenol and 16 g of potassium carbonate were added to a dimethylformamide (150 ml) solution of 15 g of 3,6-dichloro-N-(3-methyl-1,2,4-thiadiazol-5-yl)pyridine-2-carboxamide, and stirred at 50° C. for 1.5 hours. At room temperature, chloroform and water were added to it, and its pH was controlled to 3 with aqueous 2 N hydrochloric acid solution added thereto. This was extracted with chloroform, the organic layer was washed with saturated saline water, and dried with anhydrous magnesium sulfate. The solvent was evaporated away under reduced pressure, 300 ml of t-butyl methyl ether was added to the residue, and the resulting solid was taken out through filtration to obtain 14.1 g of the entitled compound as a yellow solid.

Step 3

Production of 3-[(4-hydroxyphenyl)thio]-N-(3-methyl-1,2,4-thiadiazol-5-yl)-6-[(4-methyl-4H-1,2,4-triazol-3-yl)thio]pyridine-2-carboxamide 20 g of 4-methyl-4H-1,2,4-triazole-3-thiol and 19 g of potassium t-butoxide were added to a dimethylacetamide (130 ml) solution of 13 g of 6-chloro-3-[(4-hydroxyphenyl)thio]-N-(3-methyl-1,2,4-thiadiazol-5-yl)pyridine-2-carboxamide, and stirred under heat at 160° C. for 8 hours. At room temperature, chloroform and water were added to it, and its pH was controlled to 3 with aqueous 1 N hydrochloric acid solution added thereto. This was extracted with chloroform, and the organic layer was washed with saturated saline water, and dried with anhydrous magnesium sulfate. The solvent was evaporated away under reduced pressure, and the residue was purified through silica gel column chromatography (developing solvent: chloroform/methanol) to obtain 10.0 g of the entitled compound as a yellow solid.

$^1$HNMR (DMSO-$d_6$) δ: 2.54 (3H, s), 3.64 (3H, s), 6.90 (2H, d, J=8.8 Hz), 7.01 (1H, d, J=8.8 Hz), 7.09 (1H, d, J=8.8 Hz), 7.37 (2H, d, J=8.8 Hz), 8.34 (1H, s), 8.85 (1H, s), 13.0 (1H, br).

ESI-MS (m/e): 458 [M+H]$^+$.

Reference Example 2

Production of 3-{[4-(2-methoxyethoxy)phenyl]thio}-N-(3-methyl-1,2,4-thiadiazol-5-yl)-6-[(4-methyl-4H-1,2,4-triazol-3-yl)thio]pyridine-2-carboxamide

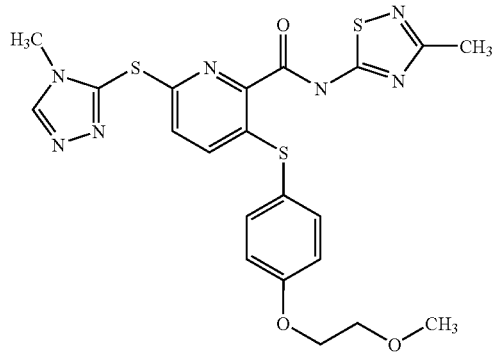

0.43 ml of 1-bromo-2-methoxyethane and 4.99 g of cesium carbonate were added to a dimethylformamide (20 ml) solution of 2 g of 3-[(4-hydroxyphenyl)thio]-N-(3-methyl-1,2,4-thiadiazol-5-yl)-6-[(4-methyl-4H-1,2,4-triazol-3-yl)thio]pyridine-2-carboxamide obtained in Reference Example (step 3), and stirred at 60° C. for 1 hour. At room temperature, aqueous saturated ammonium chloride solution was added to it, extracted with chloroform, and the organic layer was washed with saturated saline water. This was dried with anhydrous magnesium sulfate, the solvent was evaporated away under reduced pressure, and the residue was purified through silica gel column chromatography (developing solvent: chloroform/methanol) and crystallized from ethanol to obtain 1.43 g of the entitled compound as a yellow solid.

$^1$HNMR (CDCl$_3$) δ: 2.61 (3H, s), 3.47 (3H, s), 3.73 (3H, s), 3.78 (2H, t, J=4.5 Hz), 4.17 (2H, t, J=4.5 Hz), 7.02 (2H, d, J=8.8 Hz), 7.04 (1H, d, J=8.8 Hz), 7.12 (1H, d, J=8.8 Hz), 7.45 (2H, d, J=8.8 Hz), 8.41 (1H, s).

ESI-MS (m/e): 516 [M+H]$^+$.

Example 1

Production of 3-({4-[2-(dimethylamino)ethoxy]phenyl}thio)-N-(3-methyl-1,2,4-thiadiazol-5-yl)-6-[(4-methyl-4H-1,2,4-triazol-3-yl)thio]pyridine-2-carboxamide

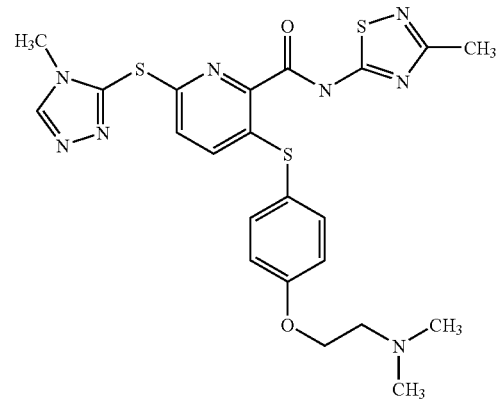

Step 1

Production of N-(3-methyl-1,2,4-thiadiazol-5-yl)-6-[(4-methyl-4H-1,2,4-triazol-3-yl)thio]-3-{[4-(2-oxoethoxy)phenyl]thio}pyridine-2-carboxamide 0.42 ml of bromoacetaldehyde diethylacetal and 1.07 g of cesium carbonate were added to a dimethylformamide (10 ml) solution of 0.5 g of 3-[(4-hydroxyphenyl)thio]-N-(3-methyl-1,2,4-thiadiazol-5-yl)-6-[(4-methyl-4H-1,2,4-triazol-3-yl)thio]pyridine-2-carboxamide obtained in Reference Example (step 3), and stirred at 90° C. for 6 hours. Aqueous saturated ammonium chloride solution was added to it at room temperature, extracted with chloroform, and the organic layer was washed with saturated saline water. This was dried with anhydrous magnesium sulfate, and the solvent was evaporated away under reduced pressure. The residue was purified through silica gel column chromatography (developing solvent: chloroform/methanol) to obtain 0.48 g of a yellow solid.

1 ml of water and 5 ml of trifluoroacetic acid were added to 0.48 g of the obtained yellow solid, and stirred at room temperature for 15 minutes. The solvent was evaporated away under reduced pressure, then chloroform and saturated saline water were added to the residue, and neutralized with aqueous sodium bicarbonate. The organic layer was dried with anhydrous magnesium sulfate. The solvent was evaporated away under reduced pressure, and the residue was purified through silica gel column chromatography (developing solvent: chloroform/methanol) to obtain 0.35 g of the entitled compound as a yellow solid.

Step 2

Production of 3-({4-[2-(dimethylamino)ethoxy]phenyl}thio)-N-(3-methyl-1,2,4-thiadiazol-5-yl)-6-[(4-methyl-4H-1,2,4-triazol-3-yl)thio]pyridine-2-carboxamide 0.25 ml of 2 M dimethylamine/tetrahydrofuran solution and 0.21 mg of sodium triacetoxyborohydride were added to a tetrahydrofuran solution of 166 mg of N-(3-methyl-1,2,4-thiadiazol-5-yl)-6-[(4-methyl-4H-1,2,4-triazol-3-yl)thio]-3-{[4-(2-oxoethoxy)phenyl]thio}pyridine-2-carboxamide obtained in the step 1, and stirred at room temperature for 30 minutes. Chloroform and saturated saline water were added to it, and extracted with chloroform. The organic layer was dried with anhydrous magnesium sulfate, the solvent was evaporated away under reduced pressure, and the residue was purified through reversed-phase middle-pressure liquid chromatography (ODS-AS-360-CC (by YMC), mobile phase: water/acetonitrile/0.1% trifluoroacetic acid). The solvent of the resulting fraction was evaporated away under reduced pressure to obtain 190 mg of the entitled compound as its trifluoroacetate. The obtained salt was neutralized, extracted with chloroform, and the organic layer was washed with saturated saline water. This was dried with anhydrous magnesium sulfate, the solvent was evaporated away under reduced pressure, and the residue was purified through partitioning thin-layer chromatography (NH-PLC05 by Fuji Silicia Chemical, chloroform/methanol=95/5) to obtain 115 mg of the entitled compound as a yellow solid.

$^1$HNMR (CDCl$_3$) δ: 2.36 (6H, s), 2.61 (3H, s), 2.77 (2H, t, J=5.5 Hz), 3.73 (3H, s), 4.11 (2H, t, J=5.5 Hz), 7.01 (2H, d, J=8.4 Hz), 7.04 (1H, d, J=8.8 Hz), 7.12 (1H, d, J=8.8 Hz), 7.44 (2H, d, J=8.4 Hz), 8.41 (1H, s).

ESI-MS (m/e): 529 [M+H]$^+$.

Example 2

Production of 3-({4-[(1-methylazetidin-3-yl)oxy]phenyl}thio)-N-(3-methyl-1,2,4-thiadiazol-5-yl)-6-[(4-methyl-4H-1,2,4-triazol-3-yl)thio]pyridine-2-carboxamide

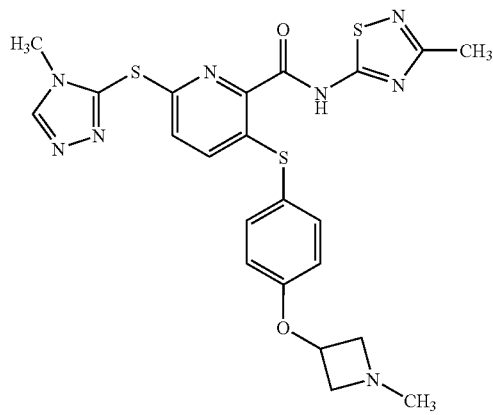

Step 1

Production of tert-butyl 3-[(methylsulfonyl)oxy]azetidine-1-carboxylate

102 μl of triethylamine and 57 μl of methanesulfonyl chloride were added to a chloroform (1 ml) solution of 107 mg of tert-butyl 3-hydroxyazetidine-1-carboxylate, and stirred at room temperature for 30 minutes. At room temperature, ethyl acetate and aqueous ammonium chloride solution were added to it, and extracted with ethyl acetate, and the organic layer was washed with water and aqueous saturated sodium hydrogencarbonate solution, and dried with anhydrous sodium sulfate. The solvent was evaporated away under reduced pressure to obtain 150 mf of a crude product of the entitled compound as a colorless oil.

Step 2

Production of 3-{[4-(azetidin-3-yloxy)phenyl]thio}-N-(3-methyl-1,2,4-thiadiazol-5-yl)-6-[(4-methyl-4H-1,2,4-triazol-3-yl)thio]pyridine-2-carboxamide 287 mg of cesium carbonate was added to a dimethylformamide (600 μl) solution of 150 mg of tert-butyl 3-[(methylsulfonyl)oxy]azetidine-1-carboxylate obtained in the step 1 and 100 mg of 3-[(4-hydroxyphenyl)thio]-N-(3-methyl-1,2,4-thiadiazol-5-yl)-6-[(4-methyl-4H-1,2,4-triazol-3-yl)thio]pyridine-2-carboxamide obtained in Reference Example (step 3), and stirred at 90° C. for 4 hours. At room temperature, aqueous saturated ammonium chloride solution was added to it, extracted with chloroform, and the organic layer was dried with anhydrous sodium sulfate. The solvent was evaporated away under reduced pressure, and the residue was purified through reversed-phase middle-pressure liquid chromatography (ODS-AS-360-CC (by YMC), mobile phase: water/acetonitrile/0.1% trifluoroacetic acid). The solvent of the resulting fraction was evaporated away to obtain 99 mg of a yellow solid. 1 ml of 4 N hydrogen chloride/dioxane solution was added to 99 mg of the obtained solid, and stirred at room temperature for 30 minutes. The solvent was evaporated away under reduced pressure, and chloroform and aqueous 1 N sodium hydroxide solution were added to the residue to make it have pH=9. Then, this was extracted with chloroform, and the organic layer was dried with anhydrous magnesium sulfate. The solvent was evaporated away to obtain 67 mg of the entitled compound as a yellow solid.

Step 3

Production of 3-({4-[(1-methylazetidin-3-yl)oxy]phenyl}thio)-N-(3-methyl-1,2,4-thiadiazol-5-yl)-6-[(4-methyl-4H-1,2,4-triazol-3-yl)thio]pyridine-2-carboxamide 0.20 ml of aqueous 37% formaldehyde solution and 0.10 ml of 0.3 M zinc chloride-sodium cyanotrihydroborate/methanol solution (J. Org. Chem. 1985, 50, 1927-1932) were added to a methanol (0.40 ml) solution of 13 mg of 3-{[4-(azetidin-3-yloxy)phenyl]thio}-N-(3-methyl-1,2,4-thiadiazol-5-yl)-6-[(4-methyl-4H-1,2,4-triazol-3-yl)thio]pyridine-2-carboxamide obtained in the step 2, and stirred at room temperature for 30 minutes. Aqueous saturated sodium hydrogencarbonate solution and saturated saline water were added to it, and extracted with chloroform. The organic layer was dried with anhydrous magnesium sulfate, the solvent was evaporated away under reduced pressure, and the residue was purified through partitioning thin-layer chromatography (NH-PLC05 (by Fuji Silicia Chemical), chloroform/methanol=95/5) to obtain 12 mg of the entitled compound as a yellow solid.

$^1$H-NMR (CDCl$_3$) δ: 2.47 (3.0H, s), 2.61 (3.0H, s), 3.19-3.25 (2.0H, m), 3.74 (3.0H, s), 3.87-3.94 (2.0H, m), 4.77-4.84

(1.0H, m), 6.86 (2.0H, d, J=8.2 Hz), 7.05 (1.0H, d, J=8.6 Hz), 7.13 (1.0H, d, J=8.6 Hz), 7.45 (2.0H, d, J=8.2 Hz), 8.44 (1.0H, s).

ESI-MS (m/e): 527 [M+H]$^+$.

Example 3

Production of N-(3-methyl-1,2,4-thiadiazol-5-yl)-6-[(4-methyl-4H-1,2,4-triazol-3-yl)thio]-3-{[4-(2-pyrrolidin-1-ylethoxy)phenyl]thio}pyridine-2-carboxamide

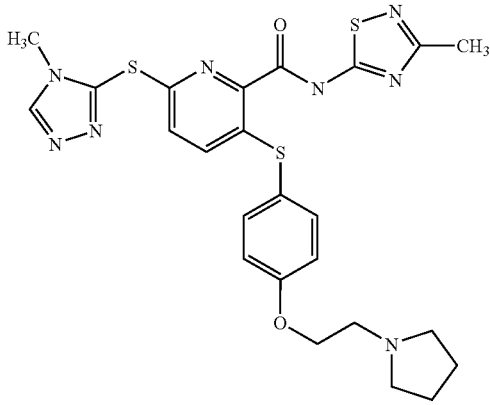

Using pyrrolidine, the entitled compound was obtained as a pale yellow solid in the same method as in Example 1 (step 2) or in accordance with the method or by combining it with an ordinary method.

$^1$HNMR (CDCl$_3$) δ: 1.85 (4H, m), 2.61 (3H, s), 2.69 (4H, m), 2.97 (2H, t, J=5.8 Hz), 3.73 (3H, s), 4.18 (2H, t, J=5.8 Hz), 7.01 (2H, d, J=8.8 Hz), 7.04 (1H, d, J=8.8 Hz), 7.12 (1H, d, J=8.8 Hz), 7.44 (2H, d, J=8.8 Hz), 8.40 (1H, s).

ESI-MS (m/e): 555 [M+H]$^+$.

Example 4

Production of 3-[(4-[2-[(2R)-2-methylpyrrolidin-1-yl]ethoxy]phenyl)thio-N-(3-methyl-1,2,4-thiadiazol-5-yl)-6-[(4-methyl-4H-1,2,4-triazol-3-yl)thio]pyridine-2-carboxamide

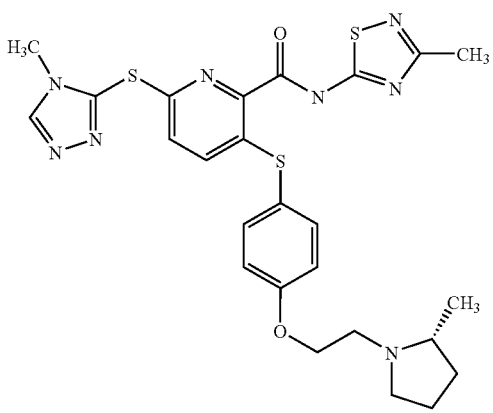

Using (R)-2-methylpyrrolidine hydrochloride, the entitled compound was obtained as a pale yellow solid in the same method as in Example 1 (step 2) or in accordance with the method or by combining it with an ordinary method.

$^1$HNMR (CDCl$_3$) δ: 1.18 (3H, d, J=6.1 Hz), 1.49 (1H, m), 1.80 (1H, m), 1.85 (1H, m), 1.97 (1H, m), 2.35 (1H, m), 2.52 (1H, m), 2.60 (1H, m), 2.61 (3H, s), 3.26 (2H, m), 3.73 (3H, s), 4.18 (2H, m), 7.00 (2H, d, J=8.8 Hz), 7.04 (1H, d, J=8.8 Hz), 7.12 (1H, d, J=8.8 Hz), 7.44 (2H, d, J=8.8 Hz), 8.41 (1H, s).

ESI-MS (m/e): 569 [M+H]$^+$.

Example 5

Production of 3-[(4-{2-[(2S)-2-methylpyrrolidin-1-yl]ethoxy}phenyl)thio-N-(3-methyl-1,2,4-thiadiazol-5-yl)-6-[(4-methyl-4H-1,2,4-triazol-3-yl)thio]pyridine-2-carboxamide

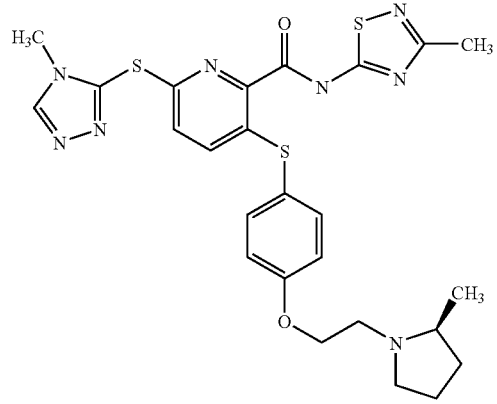

Using (S)-2-methylpyrrolidine hydrochloride, the entitled compound was obtained as a pale yellow solid in the same method as in Example 1 (step 2) or in accordance with the method or by combining it with an ordinary method.

$^1$HNMR (CDCl$_3$) δ: 1.15 (3H, d, J=6.1 Hz), 1.46 (1H, m), 1.77 (1H, m), 1.83 (1H, m), 1.96 (1H, m), 2.30 (1H, m), 2.44 (1H, m), 2.58 (1H, m), 2.62 (3H, s), 3.26 (2H, m), 3.74 (3H, s), 4.15 (2H, m), 7.00 (2H, d, J=8.8 Hz), 7.04 (1H, d, J=8.8 Hz), 7.12 (1H, d, J=8.8 Hz), 7.44 (2H, d, J=8.8 Hz), 8.41 (1H, s).

ESI-MS (m/e): 569 [M+H]$^+$.

Example 6

Production of 3-[(4-{[(2R)-1-methylpyrrolidin-2-yl]methoxy}phenyl)thio-N-(3-methyl-1,2,4-thiadiazol-5-yl)-6-[(4-methyl-4H-1,2,4-triazol-3-yl)thio]pyridine-2-carboxamide

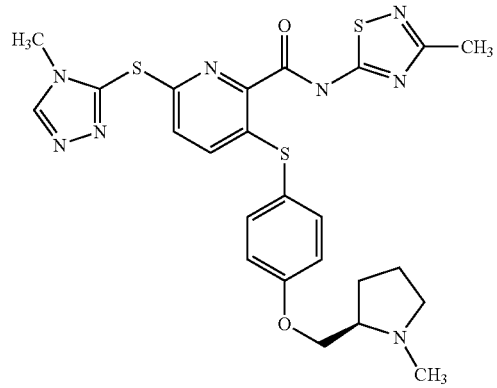

Using t-butyl (2R)-2-(hydroxymethyl)pyrrolidine-1-carboxylate (Boc-D-prolinol), the entitled compound was obtained as a pale yellow solid in the same method as in Example 2 or in accordance with the method or by combining it with an ordinary method.

¹HNMR (CDCl₃) δ: 1.82 (3H, m), 2.05 (1H, m), 2.36 (1H, m), 2.51 (3H, s), 2.61 (3H, s), 2.72 (1H, m), 3.15 (1H, m), 3.73 (3H, s), 3.94 (1H, m), 4.05 (1H, m), 7.01 (2H, d, J=8.8 Hz), 7.04 (1H, d, J=8.8 Hz), 7.12 (1H, d, J=8.8 Hz), 7.44 (2H, d, J=8.8 Hz), 8.41 (1H, s).
ESI-MS (m/e): 555 [M+H]⁺.

Example 7

Production of 3-[(4-{[(2S)-1-methylpyrrolidin-2-yl]methoxy}phenyl)thio]-N-(3-methyl-1,2,4-thiadiazol-5-yl)-6-[(4-methyl-4H-1,2,4-triazol-3-yl)thio]pyridine-2-carboxamide

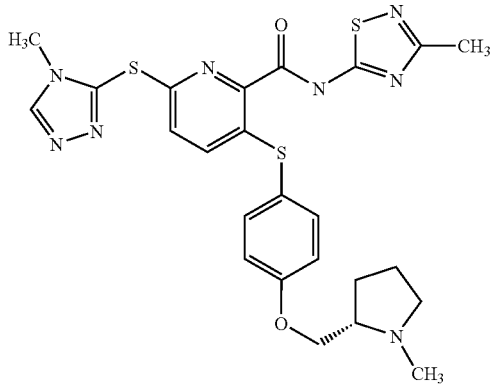

Using t-butyl (2S)-2-(hydroxymethyl)pyrrolidine-1-carboxylate (Boc-L-prolinol), the entitled compound was obtained as a pale yellow solid in the same method as in Example 2 or in accordance with the method or by combining it with an ordinary method.
¹HNMR (CDCl₃) δ: 1.82 (3H, m), 2.05 (1H, m), 2.35 (1H, m), 2.50 (3H, s), 2.61 (3H, s), 2.72 (1H, m), 3.15 (1H, m), 3.73 (3H, s), 3.94 (1H, m), 4.03 (1H, m), 7.01 (2H, d, J=8.8 Hz), 7.04 (1H, d, J=8.8 Hz), 7.12 (1H, d, J=8.8 Hz), 7.44 (2H, d, J=8.8 Hz), 8.41 (1H, s).
ESI-MS (m/e): 555 [M+H]⁺.

Example 8

Production of 3-{[4-(2-azetidin-1-ylethoxy)phenyl]thio}-N-(3-methyl-1,2,4-thiadiazol-5-yl)-6-[(4-methyl-4H-1,2,4-triazol-3-yl)thio]pyridine-2-carboxamide

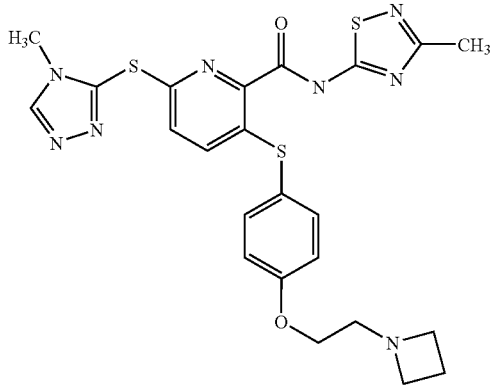

Using azetidine, the entitled compound was obtained as a pale yellow solid in the same method as in Example 1 (step 2) or in accordance with the method or by combining it with an ordinary method.

¹HNMR (CDCl₃) δ: 2.13 (2H, m), 2.61 (3H, s), 2.84 (2H, m), 3.33 (4H, m), 3.73 (3H, s), 3.99 (2H, m), 6.99 (2H, d, J=8.8 Hz), 7.03 (1H, d, J=8.8 Hz), 7.12 (1H, d, J=8.8 Hz), 7.43 (2H, d, J=8.8 Hz), 8.40 (1H, s).
ESI-MS (m/e): 541 [M+H]⁺.

Example 9

Production of 3-[(4-{[(3S)-1-methylpyrrolidin-3-yl]methoxy}phenyl)thio-N-(3-methyl-1,2,4-thiadiazol-5-yl)-6-[(4-methyl-4H-1,2,4-triazol-3-yl)thio]pyridine-2-carboxamide

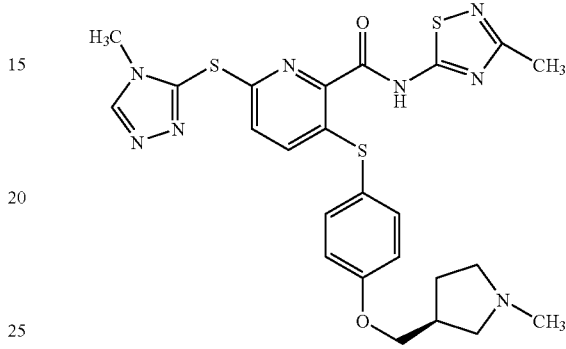

Starting from tert-butyl (3S)-3-(hydroxymethyl)pyrrolidine-1-carboxylate, the entitled compound was obtained as a pale yellow solid in the same method as in Example 2.
¹H-NMR (CDCl₃) δ: 1.59-1.70 (1.0H, m), 2.05-2.18 (1.0H, m), 2.41 (3.0H, s), 2.53-2.59 (2.0H, m), 2.62 (3.0H, s), 2.64-2.78 (3.0H, m), 3.73 (3.0H, s), 3.92-3.95 (2.0H, m), 6.98 (2.0H, d, J=8.2 Hz), 7.05 (1.0H, dd, J=8.8, 0.6 Hz), 7.12 (1.0H, dd, J=8.8, 0.6 Hz), 7.44 (2.0H, d, J=8.2 Hz), 8.40 (1.0H, s).
ESI-MS (m/e): 555 [M+H]⁺.

Example 10

Production of 3-[(4-{[(3R)-1-methylpyrrolidin-3-yl]methoxy}phenyl)thio-N-(3-methyl-1,2,4-thiadiazol-5-yl)-6-[(4-methyl-4H-1,2,4-triazol-3-yl)thio]pyridine-2-carboxamide

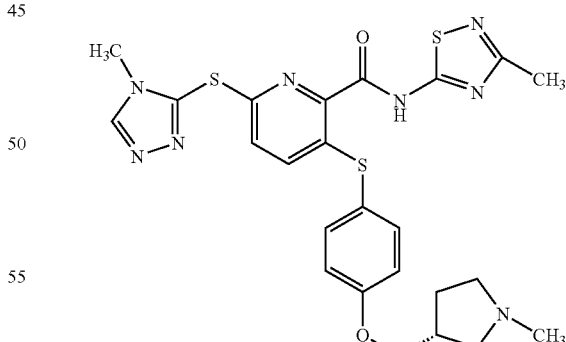

Starting from tert-butyl (3R)-3-(hydroxymethyl)pyrrolidine-1-carboxylate, the entitled compound was obtained as a yellow solid in the same method as in Example 2.
¹H-NMR (CDCl₃) δ: 1.61-1.71 (1.0H, m), 2.07-2.18 (1.0H, m), 2.42 (3.0H, s), 2.54-2.61 (2.0H, m), 2.62 (3.0H, s), 2.66-2.80 (3.0H, m), 3.73 (3.0H, s), 3.92-3.96 (2.0H, m), 6.98 (2.0H, d, J=8.4 Hz), 7.05 (1.0H, d, J=8.8 Hz), 7.12 (1.0H, d, J=8.8 Hz), 7.44 (2.0H, d, J=8.4 Hz), 8.41 (1.0H, s).
ESI-MS (m/e): 555 [M+H]⁺.

Example 11

Production of 3-[(4-{[(3S)-1-methylpyrrolidin-3-yl]oxy}phenyl)thio-N-(3-methyl-1,2,4-thiadiazol-5-yl)-6-[(4-methyl-4H-1,2,4-triazol-3-yl)thio]pyridine-2-carboxamide

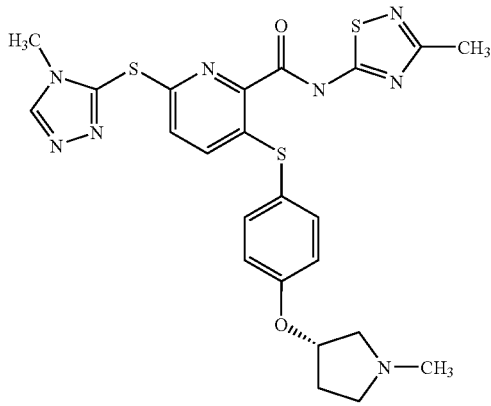

Using tert-butyl (3R)-3-hydroxypyrrolidine-1-carboxylate, the entitled compound was obtained as a pale yellow solid in the same method as in Example 2 or in accordance with the method or by combining it with an ordinary method.

$^1$HNMR (CDCl$_3$) δ: 2.04 (1H, m), 2.36 (1H, m), 2.43 (3H, s), 2.46 (1H, m), 2.61 (3H, s), 2.85 (3H, m), 3.74 (3H, s), 4.86 (1H, m), 6.94 (2H, d, J=8.8 Hz), 7.05 (1H, d, J=8.8 Hz), 7.13 (1H, d, J=8.8 Hz), 7.43 (2H, d, J=8.8 Hz), 8.41 (1H, s).

ESI-MS (m/e): 541 [M+H]$^+$.

Example 12

Production of 3-[(4-{[(3R)-1-methylpyrrolidin-3-yl]oxy}phenyl)thio-N-(3-methyl-1,2,4-thiadiazol-5-yl)-6-[(4-methyl-4H-1,2,4-triazol-3-yl)thio]pyridine-2-carboxamide

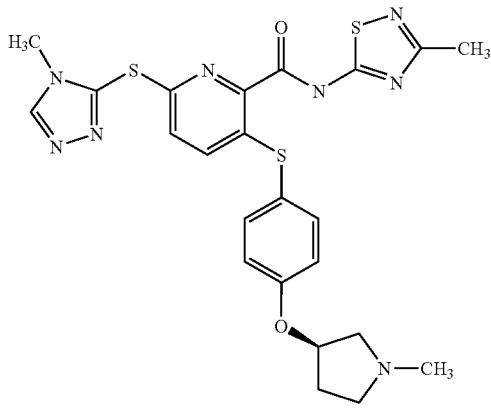

Using tert-butyl (3S)-3-hydroxypyrrolidine-1-carboxylate, the entitled compound was obtained as a pale yellow solid in the same method as in Example 2 or in accordance with the method or by combining it with an ordinary method.

$^1$HNMR (CDCl$_3$) δ: 2.04 (1H, m), 2.36 (1H, m), 2.43 (3H, s), 2.46 (1H, m), 2.61 (3H, s), 2.85 (3H, m), 3.74 (3H, s), 4.86 (1H, m), 6.94 (2H, d, J=8.8 Hz), 7.05 (1H, d, J=8.8 Hz), 7.13 (1H, d, J=8.8 Hz), 7.43 (2H, d, J=8.8 Hz), 8.41 (1H, s).

ESI-MS (m/e): 541 [M+H]$^+$.

Example 13

Production of 3-({4-[(1-methylpiperidin-4-yl)oxy]phenyl}thio)-N-(3-methyl-1,2,4-thiadiazol-5-yl)-6-[(4-methyl-4H-1,2,4-triazol-3-yl)thio]pyridine-2-carboxamide

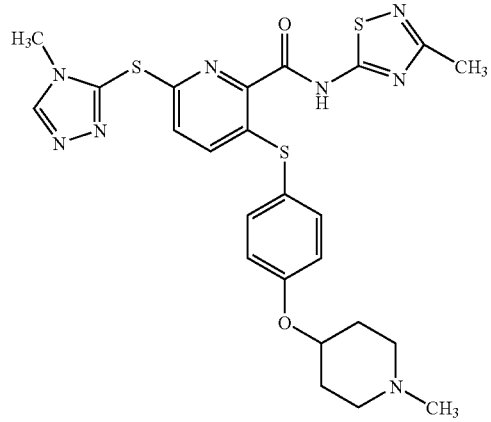

Step 1

Production of t-butyl 4-[(methylsulfonyl)oxy]piperidine-1-carboxylate

Using tert-butyl-4-hydroxypiperidine-1-carboxylate, the entitled compound was obtained as a pale yellow solid in the same method as in Example 2 or in accordance with the method or by combining it with an ordinary method.

$^1$H-NMR (CDCl$_3$) δ: 1.84-1.92 (2.0H, m), 2.01-2.08 (2.0H, m), 2.29-2.35 (2.0H, m), 2.33 (3.0H, s), 2.61 (3.0H, s), 2.68-2.76 (2.0H, m), 3.73 (3.0H, s), 4.35-4.42 (1.0H, m), 6.99 (2.0H, d, J=8.8 Hz), 7.07 (1.0H, d, J=8.8 Hz), 7.14 (1.0H, d, J=8.8 Hz), 7.43 (2.0H, d, J=8.8 Hz), 8.41 (1.0H, s).

ESI-MS (m/e): 555 [M+H]$^+$.

Example 14

Production of N-(3-methyl-1,2,4-thiadiazol-5-yl)-6-[(4-methyl-4H-1,2,4-triazol-3-yl)thio]-3-{[4-(3-pyrrolidin-1-ylpropoxy)phenyl]thio}pyridine-2-carboxamide

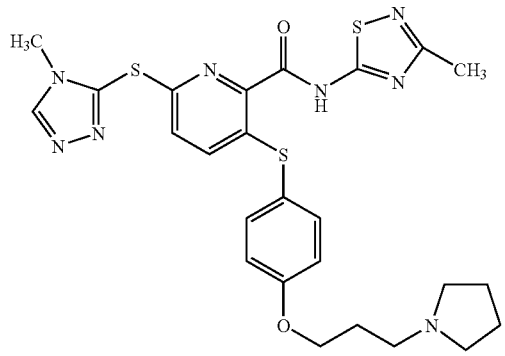

Step 1

Production of 1-(3-bromopropyl)pyrrolidine hydrobromide 1.833 g of 3-pyrrolidin-1-ylpropan-1-ol was dissolved in 8.4 ml of 5.1 M hydrogen bromide/acetic acid solution, and stirred overnight at 100° C. The solvent was evaporated away, the resulting residue was suspended in ethyl acetate, and the formed solid was taken out through filtration, washed with ethyl acetate and dried under reduced pressure. The above process was repeated three times to obtain 2.92 g of the entitled compound as a white solid.

Step 2

Production of N-(3-methyl-1,2,4-thiadiazol-5-yl)-6-[(4-methyl-4H-1,2,4-triazol-3-yl)thio]-3-{[4-(3-pyrrolidin-1-ylpropoxy)phenyl]thio}pyridine-2-carboxamide Using 19 mg of 3-[(4-hydroxyphenyl)thio]-N-(3-methyl-1,2,4-thiadiazol-5-yl)-6-[(4-methyl-4H-1,2,4-triazol-3-yl)thio]pyridine-2-carboxamide obtained in Reference Example (step 3) and 13 mg of 1-(3-bromopropyl)pyrrolidine hydrobromide obtained in the step 1, 4 mg of the entitled compound was obtained as a pale yellow solid in the same method as in Example 2 or in accordance with the method or by combining it with an ordinary method.

$^1$H-NMR (CDCl$_3$) δ: 1.79-1.84 (4.0H, m), 2.01-2.08 (2.0H, m), 2.54-2.58 (4.0H, m), 2.61 (3.0H, s), 2.66 (2.0H, t, J=7.6 Hz), 3.73 (3.0H, s), 4.08 (2.0H, t, J=6.3 Hz), 6.97-7.00 (2.0H, m), 7.05 (1.0H, d, J=8.8 Hz), 7.12 (1.0H, d, J=8.8 Hz), 7.42-7.46 (2.0H, m), 8.40 (1.0H, s).

ESI-MS (m/e): 569 [M+H]$^+$.

Example 15

Production of 3-({4-[3-(dimethylamino)propoxy]phenyl}thio)-N-(3-methyl-1,2,4-thiadiazol-5-yl)-6-[(4-methyl-4H-1,2,4-triazol-3-yl)thio]pyridine-2-carboxamide

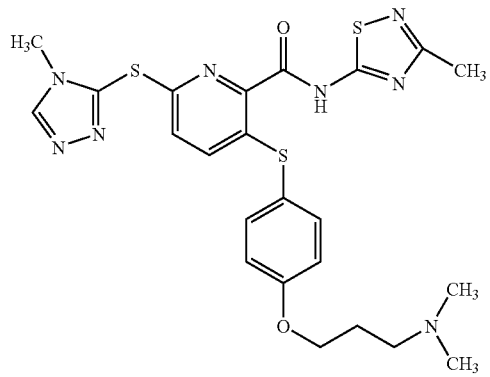

Using 2.59 g of 3-(dimethylamino)propan-1-ol, 3.4 mg of the entitled compound was obtained as a pale yellow solid in the same method as in Example 14 or in accordance with the method or by combining it with an ordinary method.

$^1$H-NMR (CDCl$_3$) δ: 1.96-2.03 (2.0H, m), 2.27 (6.0H, s), 2.48 (2.0H, t, J=7.3 Hz), 2.61 (3.0H, s), 3.73 (3.0H, s), 4.06 (2.0H, t, J=6.6 Hz), 6.97-7.01 (2.0H, m), 7.05 (1.0H, d, J=8.8 Hz), 7.12 (1.0H, d, J=8.8 Hz), 7.42-7.46 (2.0H, m), 8.40 (1.0H, s).

ESI-MS (m/e): 543 [M+H]$^+$.

Example 16

Production of 3-({4-[2-(methylamino)ethoxy]phenyl}thio)-N-(3-methyl-1,2,4-thiadiazol-5-yl)-6-[(4-methyl-4H-1,2,4-triazol-3-yl)thio]pyridine-2-carboxamide

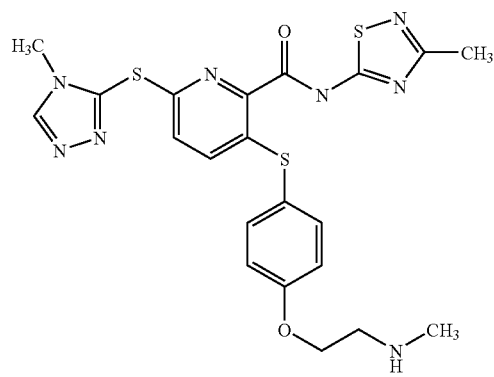

Using methylamine (2.0 M tetrahydrofuran solution), the entitled compound was obtained as a pale yellow solid in the same method as in Example 2 (step 3) or in accordance with the method or by combining it with an ordinary method.

$^1$HNMR (CDCl$_3$) δ: 2.53 (3.0H, s), 2.61 (3.0H, s), 3.02 (2.0H, t, J=5.1 Hz), 3.73 (3.0H, s), 4.12 (2.0H, t, J=5.1 Hz), 7.00 (2.0H, d, J=8.6 Hz), 7.05 (1.0H, d, J=8.8 Hz), 7.13 (1.0H, d, J=8.8 Hz), 7.45 (2.0H, d, J=8.6 Hz), 8.40 (1.0H, s).

ESI-MS (m/e): 515 [M+H]$^+$.

Example 17

Production of 3-{[4-(2-aminoethoxy)phenyl]thio}-N-(3-methyl-1,2,4-thiadiazol-5-yl)-6-[(4-methyl-4H-1,2,4-triazol-3-yl)thio]pyridine-2-carboxamide

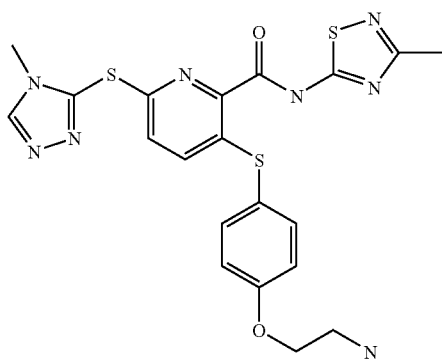

Using ammonium acetate, the entitled compound was obtained as a pale yellow solid in the same method as in Example 2 (step 3) or in accordance with the method or by combining it with an ordinary method.

$^1$HNMR (DMSO-d$_6$) δ: 2.53 (3.0H, s), 3.24 (2.0H, t, J=5.3 Hz), 3.62 (3.0H, s), 4.21 (2.0H, t, J=5.3 Hz), 7.01 (1H, d, J=8.6 Hz), 7.08-7.13 (3H, m), 7.51 (2H, d, J=8.6 Hz), 8.82 (1H, s).

ESI-MS (m/e): 501 [M+H]$^+$.

Example 18

Production of N-(3-methyl-1,2,4-thiadiazol-5-yl)-6-[(4-methyl-4H-1,2,4-triazol-3-yl)thio]-3-({4-[(3R)-pyrrolidin-3-yloxy]phenyl}thio)pyridin-2-carboxamide

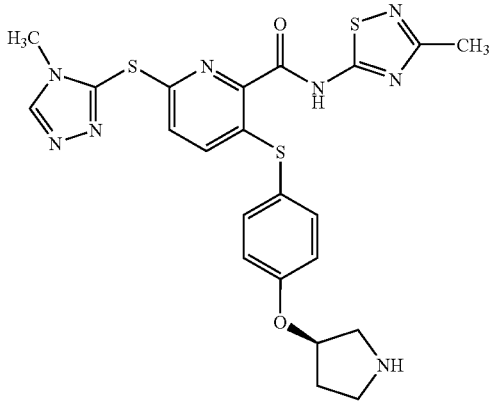

Using t-butyl (3S)-3-hydroxypyrrolidine-1-carboxylate, the entitled compound was obtained as a pale yellow solid in the same method as in Example 2 (steps 1, 2) or in accordance with the method or by combining it with an ordinary method.

$^1$H-NMR (CDCl$_3$) δ: 1.96-2.05 (1.0H, m), 2.10-2.21 (1.0H, m), 2.61 (3.0H, s), 2.81-3.62 (4.0H, m), 3.73 (3.0H, s), 4.85-4.91 (1.0H, m), 6.95 (2.0H, d, J=8.8 Hz), 7.06 (1.0H, d, J=8.7 Hz), 7.14 (1.0H, d, J=8.7 Hz), 7.44 (2.0H, d, J=8.8 Hz), 8.40 (1.0H, s).

ESI-MS (m/e): 527 [M+H]$^+$.

Example 19

Production of 3-({4-[(1-isopropylazetidin-3-yl)oxy]phenyl}thio)-N-(3-methyl-1,2,4-thiadiazol-5-yl)-6-[(4-methyl-4H-1,2,4-triazol-3-yl)thio]pyridine-2-carboxamide

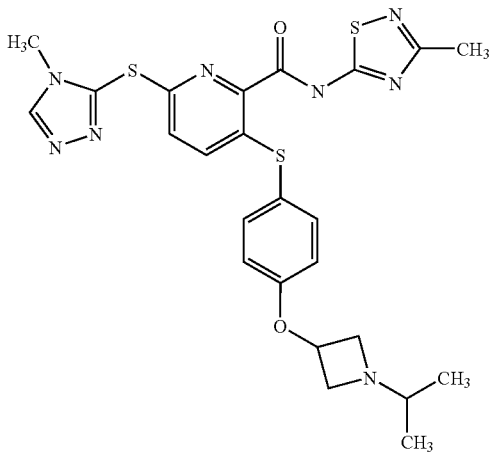

Starting from 3-{[4-(azetidin-3-yloxy)phenyl]thio}-N-(3-methyl-1,2,4-thiadiazol-5-yl)-6-[(4-methyl-4H-1,2,4-triazol-3-yl)thio]pyridine-2-carboxamide obtained in Example 2 (step 2) and using acetone, the entitled compound was obtained as a yellow solid in the same method as in Example 2 (step 3) or in accordance with the method or by combining it with an ordinary method.

$^1$H-NMR (CDCl$_3$) δ: 1.02 (6.0H, d, J=6.3 Hz), 2.44-2.52 (1.0H, m), 2.62 (3.0H, s), 3.15-3.21 (2.0H, m), 3.73 (3.0H, s), 3.86-3.92 (2.0H, m), 4.79-4.86 (1.0H, m), 6.87 (2.0H, d, J=8.3 Hz), 7.03 (1.0H, d, J=8.7 Hz), 7.14 (1.0H, d, J=8.7 Hz), 7.44 (2.0H, d, J=8.3 Hz), 8.40 (1.0H, s), 10.79-11.23 (1.0H, m).

ESI-MS (m/e): 555 [M+H]$^+$.

Example 20

Production of 3-[(4-{[(3R)-1-isopropylpyrrolidin-3-yl]oxy}phenyl)thio]-N-(3-methyl-1,2,4-thiadiazol-5-yl)-6-[(4-methyl-4H-1,2,4-triazol-3-yl)thio]pyridine-2-carboxamide

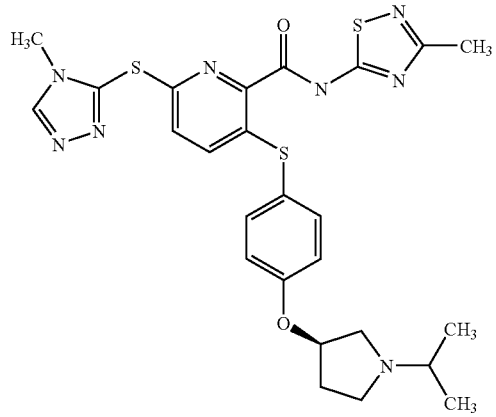

Starting from N-(3-methyl-1,2,4-thiadiazol-5-yl)-6-[(4-methyl-4H-1,2,4-triazol-3-yl)thio]-3-({4-[(3R)-pyrrolidin-3-yloxy]phenyl}thio)pyridine-2-carboxamide obtained in Example 27, the entitled compound was obtained as a pale yellow solid in the same method as in Example 19 or in accordance with the method or by combining it with an ordinary method.

$^1$H-NMR (CDCl$_3$) δ: 1.15-1.23 (6.0H, m), 1.98-3.29 (7.0H, m), 2.62 (3.0H, s), 3.73 (3.0H, s), 4.85-4.92 (1.0H, m), 6.94 (2.0H, d, J=8.5 Hz), 7.05 (1.0H, d, J=8.8 Hz), 7.14 (1.0H, d, J=8.8 Hz), 7.44 (2.0H, d, J=8.5 Hz), 8.40 (1.0H, s), 11.01 (1.0H, brs).

ESI-MS (m/e): 569 [M+H]$^+$.

Example 21

Production of N-(3-methyl-1,2,4-thiadiazol-5-yl)-6-[(4-methyl-4H-1,2,4-triazol-3-yl)thio]-3-({4-[(2-oxopyrrolidin-1-yl)methyl]phenyl}thio)pyridine-2-carboxamide

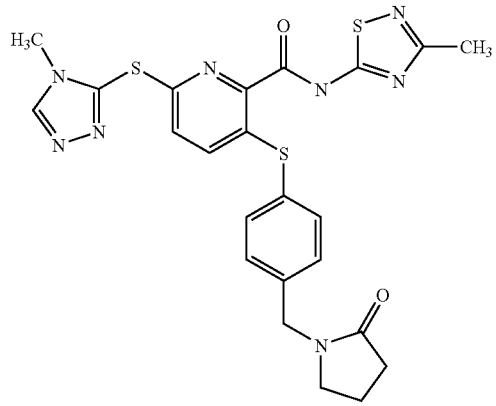

Step 1

Production of 1-[4-(methylsulfinyl)phenyl]pyrrolidin-2-one 3 g of methyl 4-aminobutyrate hydrochloride and 2.8 ml of triethylamine were added to a chloroform solution of 2 g of 4-(methylthio)benzaldehyde, and 8.4 g of sodium triacetoxyborohydride was added to it, and stirred overnight. Aqueous sodium hydrogencarbonate solution was added to it, extracted with chloroform, and the organic layer was washed with saturated saline water. This was dried with anhydrous sodium sulfate, the solvent was evaporated away under reduced pressure, and the resulting residue was purified through silica gel column chromatography to obtain 2.88 g of 1-[4-(methylthio)phenyl]pyrrolidin-2-one as a colorless oil.

With cooling with ice, 2.9 g of m-chloroperbenzoic acid was added to a chloroform (30 ml) solution of 2.88 g of the obtained oil, and stirred for 2 hours. This was diluted with chloroform, and washed with aqueous 1 N sodium hydroxide solution and saturated saline water. This was dried with anhydrous sodium sulfate, the solvent was evaporated away under reduced pressure, and the resulting residue was purified through silica gel column chromatography to obtain 3.17 g of the entitled compound as a white crystal.

Step 2

Production of 6-chloro-N-(3-methyl-1,2,4-thiadiazol-5-yl)-3-({4-[(2-oxopyrrolidin-1-yl)methyl]phenyl}thio)pyridine-2-carboxamide With cooling with ice, 0.98 ml of 2,6-lutidine and 1.16 ml of trifluoroacetic anhydride were added to a chloroform (7 ml) solution of 500 mg of 1-[4-(methylsulfinyl)phenyl]pyrrolidin-2-one obtained in the step 1, and stirred at room temperature for 1 hour. The solvent was evaporated away under reduced pressure, then 4 ml of methanol and 4 ml of triethylamine were added to the residue and heated under reflux for 30 minutes. The solvent was evaporated away, then the residue was diluted with 7 ml of dimethylformamide, and 318 mg of 3,6-dichloro-N-(3-methyl-1,2,4-thiadiazol-5-yl)pyridine-2-carboxamide obtained in Reference Example (step 1) and 290 mg of potassium carbonate were added to it, and stirred overnight at room temperature. Chloroform was added to it, neutralized with aqueous 1 N hydrochloric acid solution, and washed with saturated saline water. This was dried with anhydrous sodium sulfate, the solvent was evaporated away under reduced pressure, and the resulting residue was purified through silica gel column chromatography to obtain 360 mg of the entitled compound as a yellow solid.

Step 3

Using 6-chloro-N-(3-methyl-1,2,4-thiadiazol-5-yl)-3-({4-[(2-oxopyrrolidin-1-yl)methyl]phenyl}thio)pyridine-2-carboxamide, the entitled compound was obtained as a pale yellow solid in the same method as in Reference Example (step 3) or in accordance with the method or by combining it with an ordinary method.

$^1$HNMR (CDCl$_3$) δ: 2.07 (2H, t, J=7.4 Hz), 2.48 (2H, t, J=7.4 Hz), 2.61 (3H, s), 3.35 (2H, t, J=7.4 Hz), 3.75 (3H, s), 4.51 (2H, s, 3H), 7.04 (1H, d, J=8.8 Hz), 7.13 (1H, d, J=8.8 Hz), 7.35 (2H, d, J=8.8 Hz), 7.51 (2H, d, J=8.8 Hz), 8.43 (1H, s), 11.1 (1H, br).

ESI-MS (m/e): 539 [M+H]$^+$.

Example 22

Production of 3-([4-[2-(dimethylnitroryl)ethoxy]phenyl]thio)-N-(3-methyl-1,2,4-thiadiazol-5-yl)-6-[(4-methyl-4H-1,2,4-triazol-3-yl)thio]pyridine-2-carboxamide

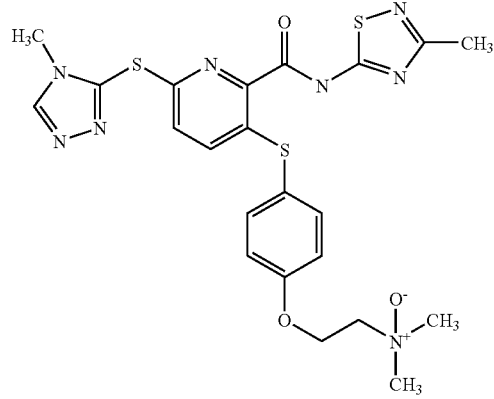

At 0° C., 9.2 mg of m-chloroperbenzoic acid was added to a chloroform solution of 20 mg of 3-({4-[2-(dimethylamino)ethoxy]phenyl}thio)-N-(3-methyl-1,2,4-thiadiazol-5-yl)-6-[(4-methyl-4H-1,2,4-triazol-3-yl)thio]pyridine-2-carboxamide obtained in Example 1, and stirred at 0° C. for 30 minutes. Aqueous sodium sulfite solution was added to it, extracted with chloroform, and the organic layer was dried with anhydrous sodium sulfate. The solvent was evaporated away under reduced pressure, and the residue was purified through reversed-phase middle-pressure liquid chromatography [ODS-AS-360-CC (by YMC), mobile phase: water/acetonitrile/0.1% trifluoroacetic acid]. The solvent of the obtained fraction was evaporated away under reduced pressure to obtain 17.5 mg of the entitled compound as a yellow solid.

$^1$HNMR (CDCl$_3$) δ: 2.61 (3H, s), 3.65 (6H, s), 3.75 (3H, s), 4.22 (2H, m), 4.60 (2H, m), 7.03 (2H, d, J=8.8 Hz), 7.04 (1H, d, J=8.8 Hz), 7.12 (1H, d, J=8.8 Hz), 7.50 (2H, d, J=8.8 Hz), 8.49 (1H, s).

ESI-MS (m/e): 545 [M+H]$^+$.

Example 23

Production of 3-[(4-{2-[ethyl(methyl)amino]ethoxy}phenyl)thio]-N-(3-methyl-1,2,4-thiadiazol-5-yl)-6-[(4-methyl-4H-1,2,4-triazol-3-yl)thio]pyridine-2-carboxamide

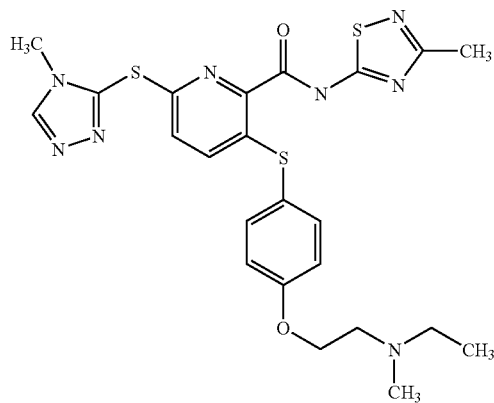

Using N-ethylmethylamine, the entitled compound was obtained as a pale yellow solid in the same method as in Example 1 (step 2) or in accordance with the method or by combining it with an ordinary method.

¹HNMR (CDCl₃) δ: 1.21 (3H, t, J=7.2 Hz), 2.37 (3H, s), 2.58 (2H, q, J=7.2 Hz), 2.61 (3H, s), 2.85 (2H, t, J=5.7 Hz), 3.73 (3H, s), 4.13 (2H, t, J=5.7 Hz), 7.00 (2H, d, J=8.8 Hz), 7.04 (1H, d, J=8.8 Hz), 7.12 (1H, d, J=8.8 Hz), 7.44 (2H, d, J=8.8 Hz), 8.41 (1H, s).
ESI-MS (m/e): 543 [M+H]⁺.

Example 24

Production of 3-({4-[2-(diethylamino)ethoxy]phenyl}thio)-N-(3-methyl-1,2,4-thiadiazol-5-yl)-6-[(4-methyl-4H-1,2,4-triazol-3-yl)thio]pyridine-2-carboxamide

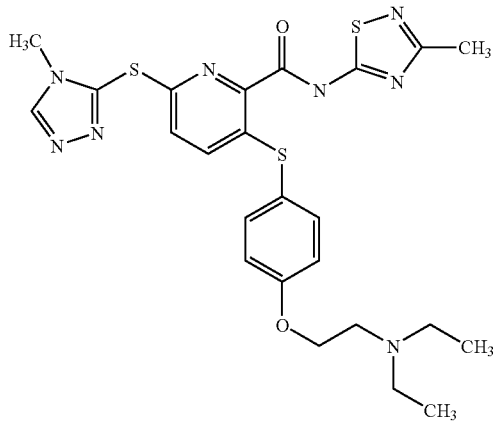

Using diethylamine, the entitled compound was obtained as a pale yellow solid in the same method as in Example 1 (step 2) or in accordance with the method or by combining it with an ordinary method.

¹HNMR (CDCl₃) δ: 1.09 (6H, t, J=7.0 Hz), 2.61 (3H, s), 2.67 (4H, q, J=7.0 Hz), 2.92 (2H, t, J=6.2 Hz), 3.73 (3H, s), 4.10 (2H, t, J=6.2 Hz), 6.99 (2H, d, J=8.8 Hz), 7.04 (1H, d, J=8.8 Hz), 7.12 (1H, d, J=8.8 Hz), 7.44 (2H, d, J=8.8 Hz), 8.41 (1H, s).
ESI-MS (m/e): 557 [M+H]⁺.

Example 25

Production of 3-({4-[(1-ethylazetidin-3-yl)oxy]phenyl}thio)-N-(3-methyl-1,2,4-thiadiazol-5-yl)-6-[(4-methyl-4H-1,2,4-triazol-3-yl)thio]pyridine-2-carboxamide

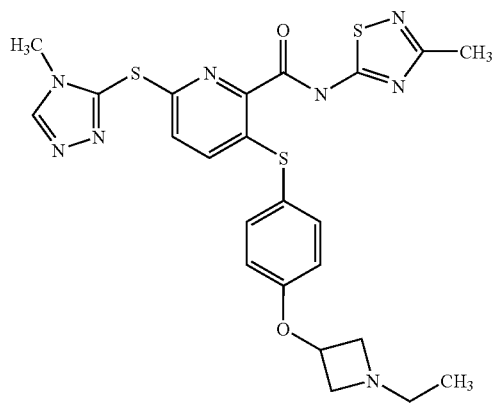

Starting from 3-{[4-(azetidin-3-yloxy)phenyl]thio}-N-(3-methyl-1,2,4-thiadiazol-5-yl)-6-[(4-methyl-4H-1,2,4-triazol-3-yl)thio]pyridine-2-carboxamide obtained in Example 2 (step 2) and using acetaldehyde, the entitled compound was obtained as a yellow solid in the same method as in Example 2 (step 3) or in accordance with the method or by combining it with an ordinary method.

¹H-NMR (CDCl₃) δ: 1.01 (3.0H, t, J=7.1 Hz), 2.57 (2.0H, q, J=7.1 Hz), 2.62 (3.0H, s), 3.09-3.14 (2.0H, m), 3.73 (3.0H, s), 3.81-3.87 (2.0H, m), 4.79-4.86 (1.0H, m), 6.86 (2.1H, d, J=8.4 Hz), 7.03 (1.0H, d, J=8.8 Hz), 7.14 (1.0H, d, J=8.8 Hz), 7.44 (2.0H, d, J=8.4 Hz), 8.40 (1.0H, s).
ESI-MS (m/e): 541 [M+H].

Example 26

Production of N-(3-methyl-1,2,4-thiadiazol-5-yl)-6-[(4-methyl-4H-1,2,4-triazol-3-yl)thio]-3-{[4-(2-piperidin-1-ylethoxy)phenyl]thio}pyridine-2-carboxamide

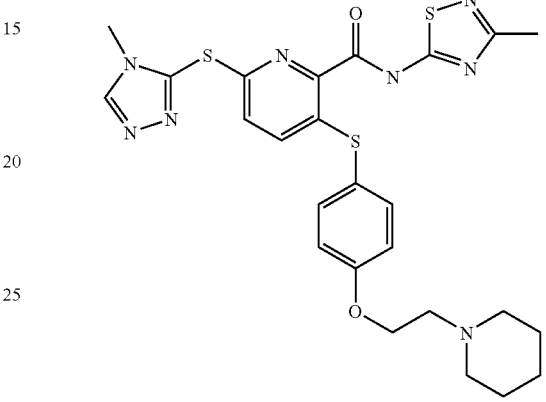

Using piperidine, the entitled compound was obtained as a pale yellow solid in the same method as in Example 1 (step 2) or in accordance with the method or by combining it with an ordinary method.

¹HNMR (CDCl₃) δ: 1.46 (2H, m), 1.63 (4H, m), 2.53 (4H, m), 2.61 (3H, s), 2.81 (2H, t, J=5.8 Hz), 3.73 (3H, s), 4.15 (2H, t, J=5.8 Hz), 6.99 (2H, d, J=8.8 Hz), 7.05 (1H, d, J=8.8 Hz), 7.12 (1H, d, J=8.8 Hz), 7.44 (2H, d, J=8.8 Hz), 8.41 (1H, s).
ESI-MS (m/e): 569 [M+H]⁺.

Example 27

Production of N-(3-methyl-1,2,4-thiadiazol-5-yl)-6-[(4-methyl-4H-1,2,4-triazol-3-yl)thio]-3-{[4-(2-morpholin-4-ylethoxy)phenyl]thio}pyridine-2-carboxamide

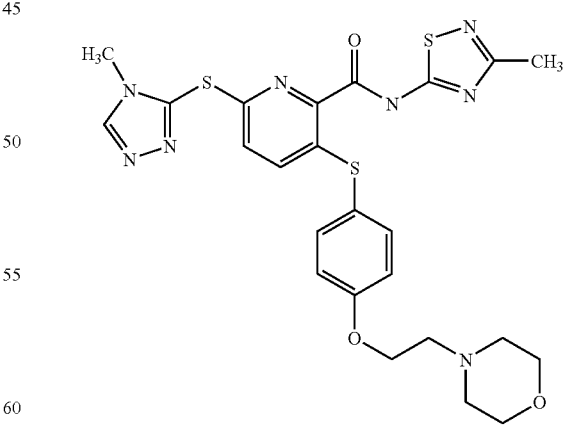

Using morpholine, the entitled compound was obtained as a pale yellow solid in the same method as in Example 1 (step 2) or in accordance with the method or by combining it with an ordinary method.

¹HNMR (CDCl₃) δ: 2.60 (4H, m), 2.61 (3H, s), 2.84 (2H, t, J=5.4 Hz), 3.74 (3H, s), 3.76 (4H, m), 4.15 (2H, t, J=5.4 Hz), 7.00 (2H, d, J=8.8 Hz), 7.04 (1H, d, J=8.8 Hz), 7.13 (1H, d, J=8.8 Hz), 7.45 (2H, d, J=8.8 Hz), 8.41 (1H, s).
ESI-MS (m/e): 571 [M+H]⁺.

Example 28

Production of 3-[(4-{[(3R)-1-ethylpyrrolidin-3-yl]oxy}phenyl)thio]-N-(3-methyl-1,2,4-thiadiazol-5-yl)-6-[(4-methyl-4H-1,2,4-triazol-3-yl)thio]pyridine-2-carboxamide

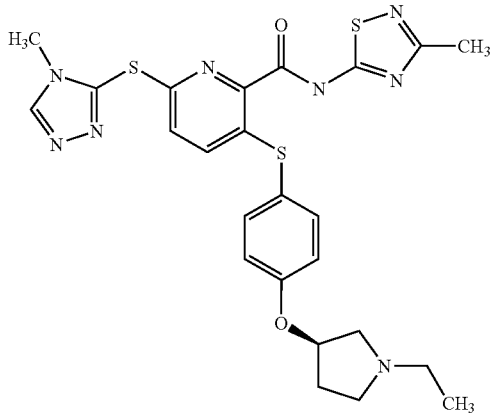

Starting from N-(3-methyl-1,2,4-thiadiazol-5-yl)-6-[(4-methyl-4H-1,2,4-triazol-3-yl)thio]-3-({4-[(3R)-pyrrolidin-3-yloxy]phenyl}thio)pyridine-2-carboxamide obtained in Example 18, the entitled compound was obtained as a pale yellow solid in the same method as in Example 25 or in accordance with the method or by combining it with an ordinary method.
¹H-NMR (CDCl₃) δ: 1.17 (3.0H, t, J=7.2 Hz), 1.98-2.08 (1.0H, m), 2.31-2.41 (1.0H, m), 2.53-2.64 (3.0H, m), 2.61 (3.0H, s), 2.83-2.97 (3.0H, m), 3.73 (3.0H, s), 4.86 (1.0H, s), 6.94 (2.0H, d, J=8.5 Hz), 7.05 (1.0H, d, J=8.8 Hz), 7.13 (1.0H, d, J=8.8 Hz), 7.43 (2.0H, d, J=8.5 Hz), 8.40 (1.0H, s).
ESI-MS (m/e): 555 [M+H]⁺.

Example 29

Production of N-(3-methyl-1,2,4-thiadiazol-5-yl)-6-[(4-methyl-4H-1,2,4-triazol-3-yl)thio]-3-{4-[2-(2-oxopyrrolidin-1-yl)ethoxy]phenyl}thio)pyridine-2-carboxamide

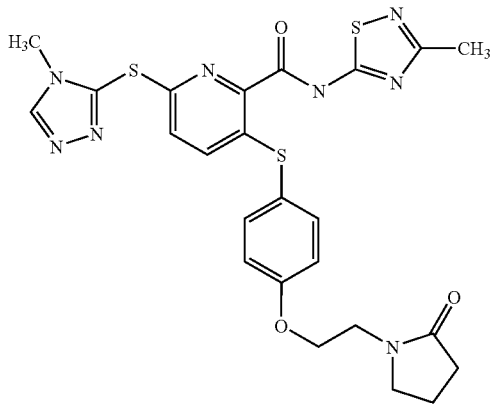

9 mg of methyl 4-aminobutyrate hydrochloride and 9 μl of triethylamine were added to a chloroform (0.3 ml) solution of 16 mg of N-(3-methyl-1,2,4-thiadiazol-5-yl)-6-[(4-methyl-4H-1,2,4-triazol-3-yl)thio]-3-{[4-(2-oxoethoxy)phenyl]thio}-pyridine-2-carboxamide obtained in Example 1 (step 1), and then 27 mg of sodium triacetoxyborohydride was added thereto, and stirred overnight. Saturated saline water was added to it, extracted with chloroform, and dried with anhydrous sodium sulfate. The solvent was evaporated away under reduced pressure, and the residue was purified through reversed-phase middle-pressure liquid chromatography [ODS-AS-360-CC (by YMC), mobile phase: water/acetonitrile/0.1% trifluoroacetic acid]. The solvent of the obtained fraction was evaporated away under reduced pressure to obtain 10.8 mg of the entitled compound as a yellow solid.
¹HNMR (CDCl₃) δ: 2.05 (2H, m), 2.41 (2H, m), 2.62 (3H, s), 3.60 (2H, m), 3.72 (2H, m), 3.74 (3H, s), 4.16 (2H, m), 6.98 (2H, d, J=8.8 Hz), 7.04 (1H, d, J=8.8 Hz), 7.13 (1H, d, J=8.8 Hz), 7.45 (2H, d, J=8.8 Hz), 8.41 (1H, s), 11.0 (1H, br).
ESI-MS (m/e): 569 [M+H]⁺.

Example 30

Production of 3-[(4-{2-[(2R)-2-methyl-1-oxidopyrrolidin-1-yl]ethoxy}phenyl)thio]-N-(3-methyl-1,2,4-thiadiazol-5-yl)-6-[(4-methyl-4H-1,2,4-triazol-3-yl)thio]pyridine-2-carboxamide

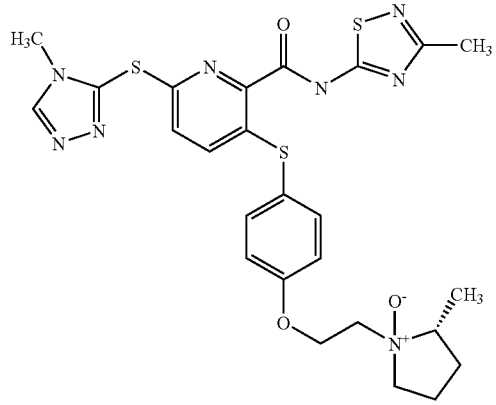

Using 3-[(4-{2-[(2R)-2-methylpyrrolidin-2-yl]ethoxy}phenyl)thio]-N-(3-methyl-1,2,4-thiadiazol-5-yl)-6-[(4-methyl-4H-1,2,4-triazol-3-yl)thio]pyridine-2-carboxamide obtained in Example 4, the entitled compound was obtained as a pale yellow solid in the same method as in Example 22 or in accordance with the method or by combining it with an ordinary method.
¹HNMR (CDCl₃) δ: 1.56 (3H, d, J=6.5 Hz), 2.04-2.20 (2H, m), 2.25-2.40 (2H, m), 2.61 (3H, s), 3.75 (3H, s), 3.70-3.80 (3H, m), 4.30-4.48 (3H, m), 4.86 (1H, m), 7.00-7.14 (4H, m), 7.48 (2H, d, J=8.4 Hz), 8.51 (1H, s).
ESI-MS (m/e): 585 [M+H]⁺.

What is claimed is:
1. A compound which is:
3-({4-[2-(dimethylamino)ethoxy]phenyl}thio)-N-(3-methyl-1,2,4-thiadiazol-5-yl)-6-[(4-methyl-4H-1,2,4-triazol-3-yl)thio]pyridin-2-carboxamide, or a pharmaceutically acceptable salt thereof.
2. A pharmaceutical composition comprising a compound in accordance with claim 1, or a pharmaceutically acceptable salt thereof, in combination with a pharmaceutical acceptable carrier.
3. A method of treating type 2 diabetes in a mammalian patient in need of such treatment comprising administering to the patient a compound in accordance with claim 1, or a pharmaceutically salt thereof, in an amount that is effective to treat type 2 diabetes.

* * * * *

UNITED STATES PATENT AND TRADEMARK OFFICE
CERTIFICATE OF CORRECTION

| | |
|---|---|
| PATENT NO. | : 8,338,460 B2 |
| APPLICATION NO. | : 11/973240 |
| DATED | : December 25, 2012 |
| INVENTOR(S) | : Hashimoto et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1157 days.

Signed and Sealed this
Eighteenth Day of November, 2014

Michelle K. Lee
*Deputy Director of the United States Patent and Trademark Office*